United States Patent
Akashi

(10) Patent No.: US 10,862,050 B2
(45) Date of Patent: Dec. 8, 2020

(54) HETEROCYCLIC COMPOUND AND ORGANIC ELECTROLUMINESCENCE DEVICE INCLUDING THE SAME

(71) Applicant: SAMSUNG DISPLAY CO., LTD., Yongin-si (KR)

(72) Inventor: Nobutaka Akashi, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 278 days.

(21) Appl. No.: 15/941,061

(22) Filed: Mar. 30, 2018

(65) Prior Publication Data

US 2018/0331303 A1  Nov. 15, 2018

(30) Foreign Application Priority Data

May 15, 2017  (KR) .......................... 10-2017-0060153

(51) Int. Cl.
*H01L 51/50* (2006.01)
*H01L 51/00* (2006.01)
(Continued)

(52) U.S. Cl.
CPC ........ *H01L 51/0072* (2013.01); *C07D 487/06* (2013.01); *C07D 519/00* (2013.01);
(Continued)

(58) Field of Classification Search
None
See application file for complete search history.

(56) References Cited

U.S. PATENT DOCUMENTS 9,708,262 B2  7/2017  Parham et al.
9,711,735 B2  7/2017  Yang et al.
(Continued)

FOREIGN PATENT DOCUMENTS

KR  10-2012-0129922 A  11/2012
KR  10-2015-0002219 A  1/2015
(Continued)

*Primary Examiner* — Gregory D Clark
(74) *Attorney, Agent, or Firm* — Lewis Roca Rothgerber Christie LLP

(57) ABSTRACT

A heterocyclic compound is represented by Formula 1 and has an absolute value of a difference between a singlet energy level and a triplet energy level of about 0.2 eV or less:

[Formula 1]

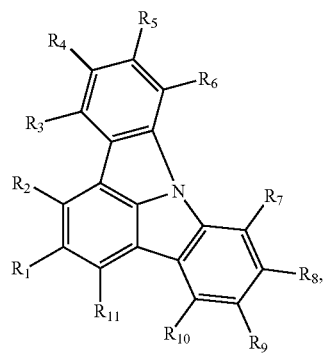

wherein in Formula 1, at least one of $R_1$ to $R_{11}$ is represented by Formula 2.

(Continued)

[Formula 2]

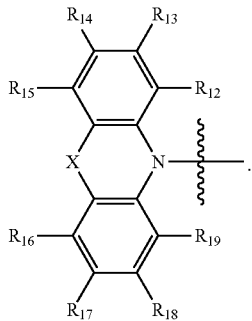

20 Claims, 1 Drawing Sheet

(51) Int. Cl.
C07D 487/06 (2006.01)
C09K 11/06 (2006.01)
C07D 519/00 (2006.01)
C07F 7/08 (2006.01)

(52) U.S. Cl.
CPC ............ *C07F 7/0816* (2013.01); *C09K 11/06* (2013.01); *H01L 51/0059* (2013.01); *H01L 51/0094* (2013.01); *C09K 2211/1018* (2013.01); *H01L 51/0071* (2013.01); *H01L 51/5012* (2013.01); *H01L 51/5024* (2013.01); *H01L 51/5056* (2013.01); *H01L 51/5072* (2013.01); *H01L 51/5088* (2013.01); *H01L 51/5092* (2013.01); *H01L 51/5096* (2013.01)

(56) References Cited

U.S. PATENT DOCUMENTS

2015/0333273 A1 11/2015 Lee et al.
2016/0260908 A1 9/2016 Zeng et al.
2016/0293853 A1 9/2016 Zeng et al.
2017/0092875 A1 3/2017 Parham et al.

FOREIGN PATENT DOCUMENTS

| KR | 10-2015-0131564 A | | 11/2015 | |
|---|---|---|---|---|
| KR | 10-2016-26101 | * | 3/2016 | ............ C09K 11/06 |
| KR | 10-2016-0045569 A | | 4/2016 | |
| KR | 10-2016-0045570 A | | 4/2016 | |
| KR | 10-2016-0133545 A | | 11/2016 | |
| WO | WO 2011/088877 A1 | | 7/2011 | |

* cited by examiner

HETEROCYCLIC COMPOUND AND ORGANIC ELECTROLUMINESCENCE DEVICE INCLUDING THE SAME

CROSS-REFERENCE TO RELATED APPLICATION

Korean Patent Application No. 10-2017-0060153, filed on May 15, 2017, in the Korean Intellectual Property Office, and entitled: "Heterocyclic Compound and Organic Electroluminescence Device Including the Same," is incorporated by reference herein in its entirety.

BACKGROUND

1. Field

The present disclosure herein relates to a heterocyclic compound and an organic electroluminescence device including the same.

2. Description of the Related Art

The development of an organic electroluminescence display as an image display is being actively conducted. An organic electroluminescence display is different from a liquid crystal display in that the organic electroluminescence display is a self-luminescent display produces an image via the recombination of holes and electrons injected from a first electrode and a second electrode in an emission layer and via light emission from a luminescent material including an organic compound in the emission layer.

SUMMARY

Embodiments are directed to a heterocyclic compound represented by the following Formula 1, wherein an absolute value of a difference between a singlet energy level and a triplet energy level of about 0.2 eV or less:

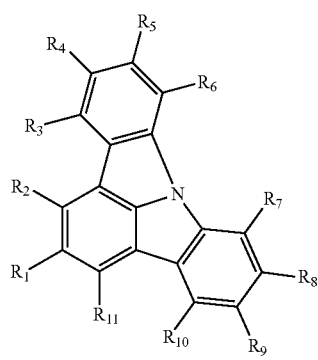

[Formula 1]

In Formula 1, $R_1$ to $R_{11}$ are each independently a hydrogen atom, a deuterium atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring, and at least one of $R_1$ to $R_{11}$ is represented by the following Formula 2:

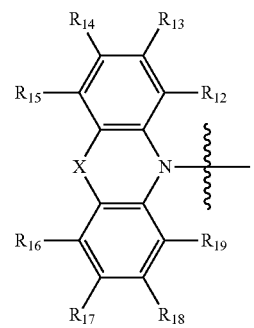

[Formula 2]

In Formula 2, X may be $CY_1Y_2$, $SiY_3Y_4$, $NY_5$, O or S. $Y_1$ to $Y_5$, and $R_{12}$ to $R_{19}$ may each independently be a hydrogen atom, a deuterium atom, a halogen atom, a cyano group, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring, and $Y_1$ and $Y_2$, and $Y_3$ and $Y_4$ may be combined with each other to form a hydrocarbon ring or a heterocycle.

Formula 2 may be represented by one of the following Formulae 2-1 to 2-3:

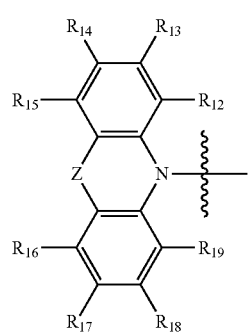

[Formula 2-1]

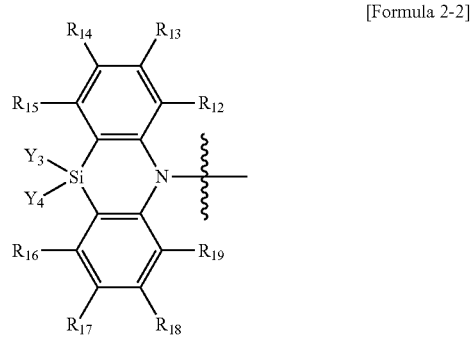

[Formula 2-2]

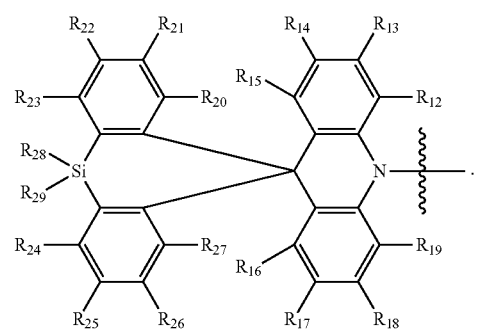

[Formula 2-3]

In Formula 2-1, Z may be $CY_1Y_2$, $NY_5$, O, or S. In Formula 2-3, the definition of $R_{20}$ to $R_{29}$ may be the same as that of $R_{12}$ to $R_{19}$, and $R_{28}$ and $R_{29}$ may be combined with each other to form a hydrocarbon ring or a heterocycle. In Formula 2-1 to Formula 2-3, $R_{12}$ to $R_{19}$, and $Y_1$ to $Y_5$ are the same as described above.

In an embodiment, one of $R_1$, $R_4$, or $R_5$ may be represented by Formula 2.

In an embodiment, Formula 1 may be represented by the following Formula 1-1:

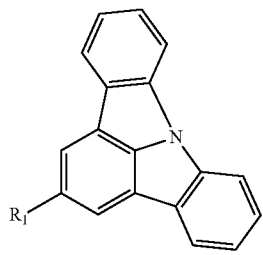

[Formula 1-1]

In Formula 1-1, $R_1$ is represented by Formula 2.

In an embodiment, Formula 1 may be represented by the following Formula 1-2:

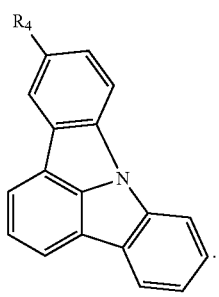

[Formula 1-2]

In Formula 1-2, $R_4$ may be represented by Formula 2.

In an embodiment, Formula 1 may be represented by the following Formula 1-3:

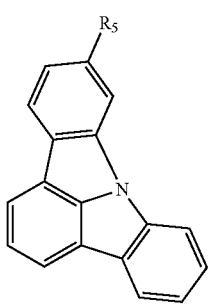

[Formula 1-3]

In Formula 1-3, $R_5$ is represented by Formula 2.

In an embodiment, Formula 2 may be represented by one of the following Formulae 2-4 to 2-7:

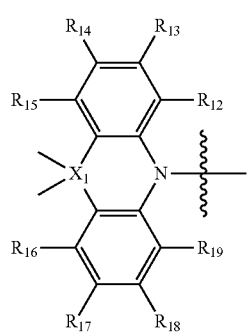

[Formula 2-4]

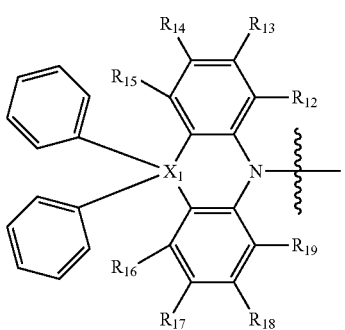

[Formula 2-5]

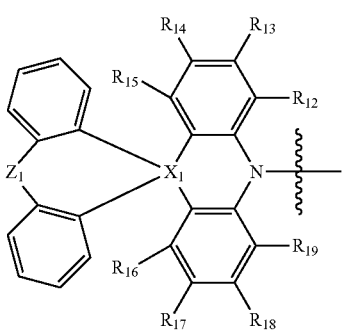

[Formula 2-6]

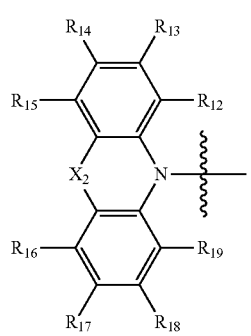

[Formula 2-7]

In Formulae 2-4 to 2-7, $X_1$ may be C or Si, $X_2$ may be O or S. $Z_1$ may be a direct linkage, O, or S, and $R_{12}$ to $R_{19}$ are the same as described above.

In an embodiment, Formula 2 may be represented by one of the following Formulae 2-8 to 2-10:

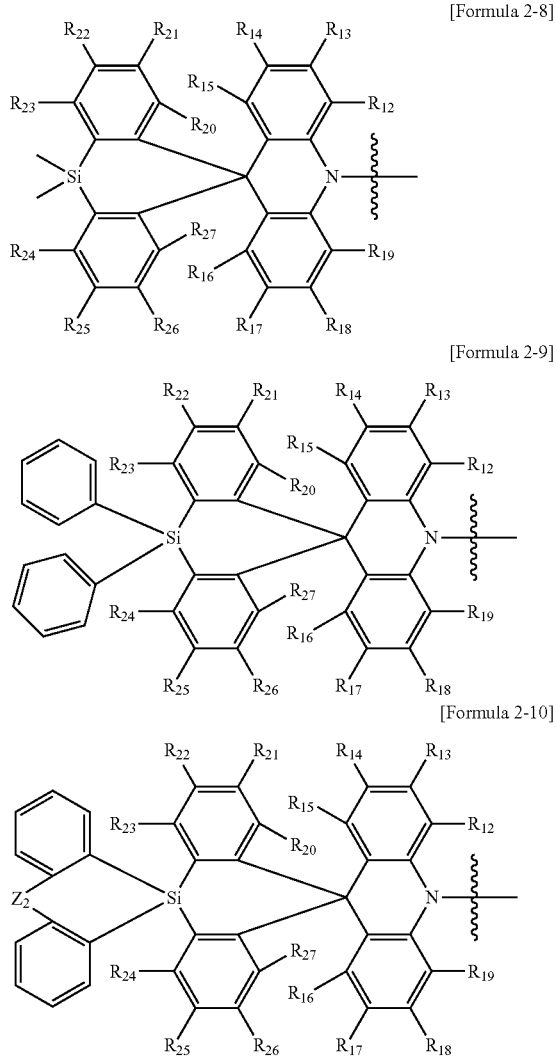

[Formula 2-8]

[Formula 2-9]

[Formula 2-10]

In Formulae 2-8 to 2-10, $Z_2$ may be a direct linkage, O, or S. The definition of $R_{20}$ to $R_{29}$ may be the same as that of $R_{12}$ to $R_{19}$. The definition of $R_{12}$ to $R_{19}$ may be the same as described above.

An organic electroluminescence device may include a first electrode, a hole transport region provided on the first electrode, an emission layer provided on the hole transport region, an electron transport region provided on the emission layer, and a second electrode provided on the electron transport region, wherein the first electrode and the second electrode each independently comprise at least one selected from Ag, Mg, Cu, Al, Pt, Pd, Au, Ni, Nd, Ir, Cr, Li, Ca, LiF/Ca, LiF/Al, Mo, Ti, In, Sn, and Zn, a compound of two or more thereof, a mixture of two or more thereof, and an oxide thereof, wherein the emission layer includes the heterocyclic compound according to an embodiment.

The heterocyclic compound may be a material for emitting thermally activated delayed fluorescence.

BRIEF DESCRIPTION OF THE DRAWINGS

Features will become apparent to those of skill in the art by describing in detail exemplary embodiments with reference to the attached drawings in which.

DETAILED DESCRIPTION

Figure 1:
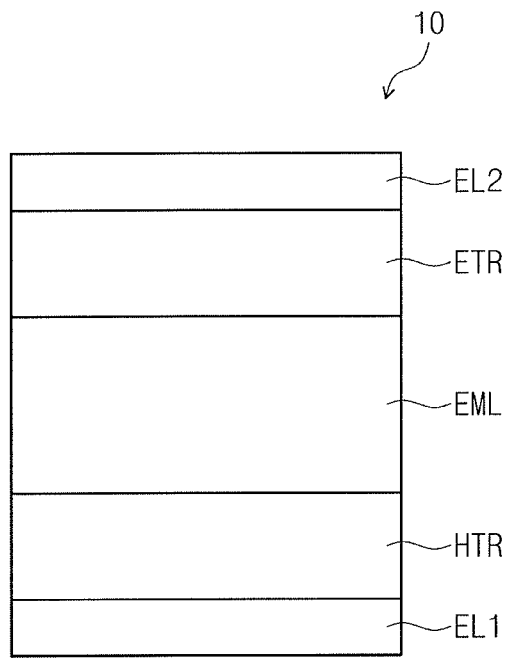
FIG. 1 illustrates a cross-sectional view schematically depicting an organic electroluminescence device according to an embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present. Further, it will be understood that when a layer is referred to as being "between" two layers, it can be the only layer between the two layers, or one or more intervening layers may also be present. Like reference characters refer to like elements.

In the present disclosure,

in a reproduced portion of a formula represents a connection to a remaining portion of the formula.

In the present disclosure, "substituted or unsubstituted" may refer to substituted with at least one substituent selected from the group consisting of a deuterium atom, a halogen atom, a cyano group, a nitro group, an amino group, a silyl group, a boron group, a phosphine oxide group, a phosphine sulfide group, an alkyl group, an alkenyl group, an aryl group, and a heterocycle, or unsubstituted. In addition, each of the substituent illustrated above may be substituted or unsubstituted. For example, a biphenyl group may be interpreted as an aryl group, or a phenyl group substituted with a phenyl group.

In the present disclosure, the term "forming a ring by combining with each other" may refer to forming substituted or unsubstituted hydrocarbon ring, or substituted or unsubstituted heterocycle by combining adjacent groups with each other. The cyclic hydrocarbon may include aliphatic cyclic hydrocarbon and aromatic cyclic hydrocarbon. The heterocycle may include aliphatic heterocycle and aromatic heterocycle. The cyclic hydrocarbon and heterocycle may be a monocycle or polycycle. In addition, the ring formed by combining with an adjacent group may be connected with another ring to form a spiro structure.

In the present disclosure, a halogen atom may include a fluorine atom, a chlorine atom, a bromine atom, or an iodine atom.

In the present disclosure, an alkyl group may have a linear or branched chain shape or a cyclic shape. The carbon number of the alkyl group may be, for example, 1 to 30, 1 to 20, 1 to 10, or 1 to 6. Examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldodecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyl eicosyl, 2-butyl eicosyl, 2-hexyl eicosyl, 2-octyl eicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., groups.

In the present disclosure, the term "aryl" refers to an optional functional group or substituent derived from aromatic cyclic hydrocarbon. The aryl group may be monocyclic aryl or polycyclic aryl. The ring carbon number of the aryl group may be, for example, 6 to 30, 6 to 20, or 6 to 15. Examples of the aryl group may include phenyl, naphthyl, fluorenyl, anthracenyl, phenanthryl, biphenyl, terphenyl, quaterphenyl, quinqphenyl, sexiphenyl, biphenylene, triphenylene, pyrenyl, benzofluoranthenyl, chrysenyl, etc., groups. a In the present disclosure, fluorenyl group may be substituted, or two substituents may be combined with each other to form a spiro structure. Examples of a substituted fluorenyl group include the following.

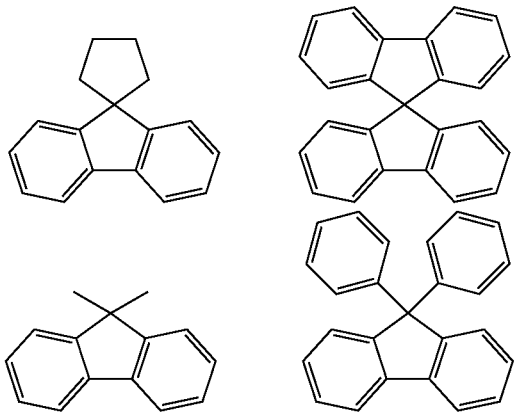

In the present disclosure, the term "heteroaryl" may refer to a heteroaryl group including at least one of O, N, P, Si or S as a heteroatom. When the heteroaryl group includes two heteroatoms, two heteroatoms may be the same or different from each other. The ring carbon number of the heteroaryl group may be, for example, 2 to 30, or 2 to 20. The heteroaryl group may be monocyclic heteroaryl group or polycyclic heteroaryl group. The polycyclic heteroaryl group may have a structure, for example, including two rings or three rings. Examples of the heteroaryl group may include thiophene, furan, pyrrole, imidazole, thiazole, oxazole, oxadiazole, triazole, pyridyl, bipyridyl, pyrimidyl, triazine, triazole, acridyl, pyridazine, pyrazinyl, quinolinyl, quinazoline, quinoxalinyl, phenoxazyl, phthalazinyl, pyrido pyrimidinyl, pyrido pyrazinyl, pyrazino pyrazinyl, isoquinoline, indole, carbazole, N-arylcarbazole, N-heteroaryl carbazole, N-alkyl carbazole, benzoxazole, benzoimidazole, benzothiazole, benzocarbazole, benzothiophene, dibenzothiophene, thienothiophene, benzofuranyl, phenanthroline, thiazolyl, isooxazolyl, oxadiazolyl, thiadiazolyl, benzothiazolyl, phenothiazinyl, dibenzosilole, dibenzofuranyl, etc., groups.

In the present disclosure, the term "silyl group" may refer to, for example, an alkylsilyl group or an arylsilyl group. Examples of a silyl group may include trimethylsilyl, triethylsilyl, t-butyldimethylsilyl, vinyldimethylsilyl, propyldimethylsilyl, triphenylsilyl, diphenylsilyl, phenylsilyl, etc., groups.

In the present disclosure, the term "boron group" may include alkyl boron groups or aryl boron groups. Examples of the boron group may include trimethylboron, triethylboron, t-butyldimethyl boron, triphenylboron, diphenylboron, phenylboron, etc., groups.

In the present disclosure, an alkenyl group may be linear or branched. The carbon number of an alkenyl group may be, for example, 2 to 30, 2 to 20, or 2 to 10. Examples of the alkenyl group may include vinyl, 1-butenyl, 1-pentenyl, 1,3-butadienyl aryl, styrenyl, styrylvinyl, etc., groups.

In the present disclosure, the carbon number of an amino group may be, for example, 1 to 30. The amino group may include an alkylamino group and an arylamino group. Examples of the amino group may include a methylamino group, a dimethylamino group, a phenylamino group, a diphenylamino group, a naphthylamino group, a 9-methylanthracenylamino group, a triphenylamino group, etc.

In the present disclosure, the term "direct linkage" may include a single bond.

First, the heterocyclic compound according to an embodiment will be explained.

The heterocyclic compound according to an embodiment is represented by Formula 1 below.

[Formula 1]

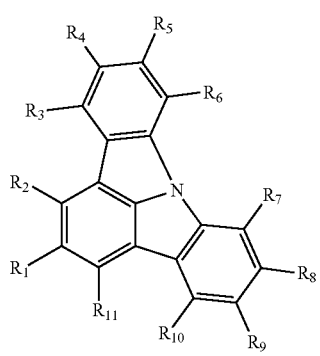

In Formula 1, $R_1$ to $R_{11}$ may each independently be a hydrogen atom, a deuterium atom, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, provided that at least one of $R_1$ to $R_{11}$ is represented by Formula 2 below.

[Formula 2]

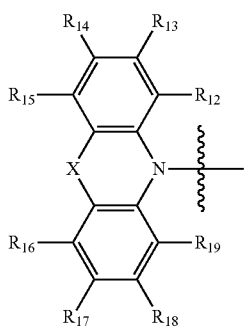

In Formula 2, X may be $CY_1Y_2$, $SiY_3Y_4$, $NY_5$, O or S. $Y_1$ to $Y_5$, and $R_{12}$ to $R_{19}$ may each independently be a hydrogen atom, a deuterium atom, a halogen atom, a cyano group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, and $Y_1$ and $Y_2$, and $Y_3$ and $Y_4$ may be combined with each other to form a hydrocarbon ring or a heterocycle. The hydrocarbon ring or the heterocycle may be substituted or unsubstituted. The heterocycle may include, for example, a heteroatom such as O and/or S.

The heterocyclic compound according to an embodiment may have an absolute value of a difference between a singlet energy level and a triplet energy level of about 0.2 eV.

The heterocyclic compound according to an embodiment may be used as a material for thermally activated delayed fluorescence. The heterocyclic compound according to an embodiment may include an electron acceptor and an electron donor in a compound. For example, the unit represented by Formula 1 may be an electron acceptor, and the unit represented by Formula 2 may be an electron donor. In the heterocyclic compound according to an embodiment, an electron acceptor and an electron donor may be connected by a direct linkage.

In Formula 1, one of $R_1$ to $R_{11}$ may be represented by Formula 2. For example, one of $R_1$, $R_4$, or $R_5$ may be represented by Formula 2.

Formula 1 may be represented by, for example, one of Formulae 1-1 to 1-3 below.

[Formula 1-1]

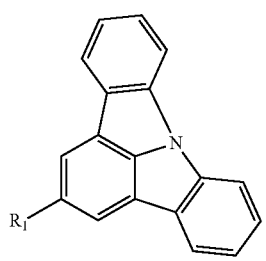

[Formula 1-2]

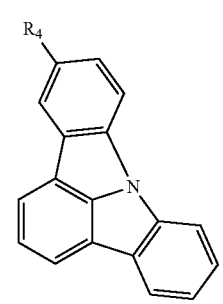

[Formula 1-3]

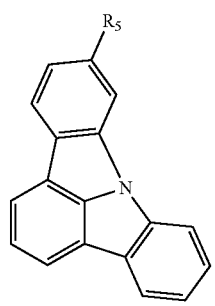

In Formula 1-1, $R_1$ may be represented by Formula 2. In Formula 1-2, $R_4$ may be represented by Formula 2. In Formula 1-3, $R_5$ is represented by Formula 2.

The indolocarbazole core in the heterocyclic compound represented by Formulae 1-1 to 1-3 may be substituted or unsubstituted at positions other than the position where substitution with Formula 2 occurs.

Formula 2, which acts as an electron donor, may particularly be represented by one of Formulae 2-1 to 2-3 below.

[Formula 2-1]

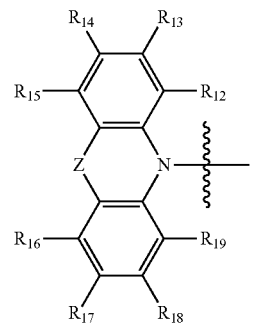

[Formula 2-2]

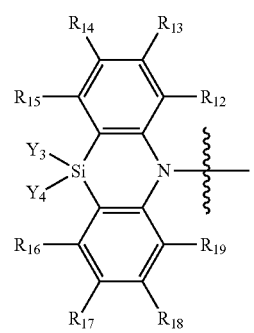

[Formula 2-3]

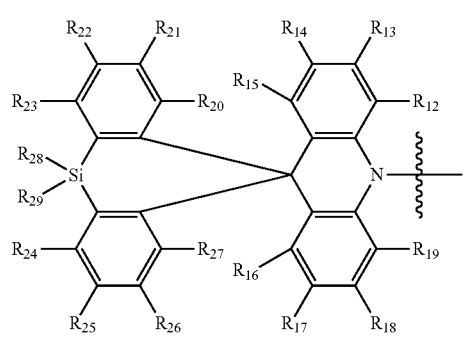

In Formula 2-1, Z may be $CY_1Y_2$, $NY_5$, O, or S. In Formula 2-3, the definition of $R_{20}$ to $R_{29}$ is the same as that of $R_{12}$ to $R_{19}$. $R_{28}$ and $R_{29}$ may be combined with each other to form a hydrocarbon ring or a heterocycle. The hydrocarbon ring or the heterocycle may be substituted or unsubstituted. In Formula 2-1 to Formula 2-3, $R_{12}$ to $R_{19}$, and $Y_1$ to $Y_5$ are the same as described above.

In Formula 2-1, $R_{14}$ and $R_{17}$ may each independently be a substituted or unsubstituted alkyl group having 1 to 10 carbon atoms. In Formula 2-1, $R_{14}$ and $R_{17}$ may be, for example, a methyl group. In Formula 2-2, $R_{14}$ and $R_{17}$ may each independently be a substituted or unsubstituted alkyl group having 1 to 10 carbon atoms. In Formula 2-2, $R_{14}$ and $R_{17}$ may be, for example, a methyl group.

In Formula 2-2, $Y_3$ and $Y_4$ may be the same. In some implementations, $Y_3$ and $Y_4$ in Formula 2-2 may be combined with each other to form a fluorene ring or a heterocycle. The heteroatom of the heterocycle may be, for example, O or S.

In Formula 2-3, $R_{14}$ and $R_{17}$ may each independently be a substituted or unsubstituted alkyl group having 1 to 10 carbon atoms. In Formula 2-3, $R_{14}$ and $R_{17}$ may be, for example, a methyl group.

In Formula 2-3, $R_{28}$ and $R_{29}$ may be the same. In some implementations, $R_{28}$ and $R_{29}$ in Formula 2-3 may be combined with each other to form a fluorene ring or a heterocycle. The heteroatom of the heterocycle may be, for example, O or S.

Formula 2 may be represented by, for example, one of Formulae 2-4 to 2-7 below.

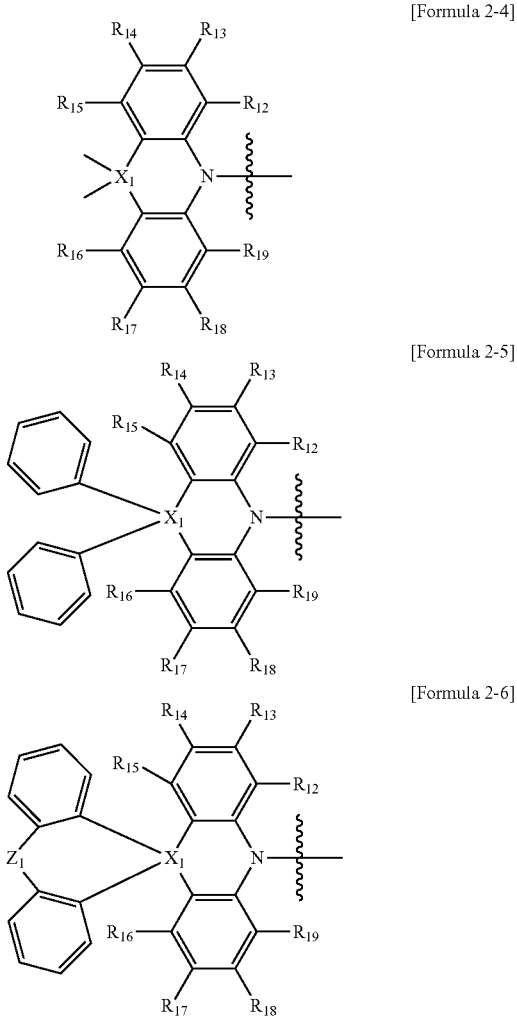

[Formula 2-4]

[Formula 2-5]

[Formula 2-6]

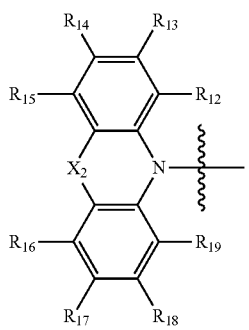

[Formula 2-7]

In Formulae 2-4 to 2-7, $X_1$ may be C or Si. $X_2$ may be O or S. $Z_1$ may be a direct linkage, O, or S. $R_{12}$ to $R_{19}$ are the same as described above.

In Formula 2-4, each of $R_{12}$ to $R_{19}$ may be a hydrogen atom. In some implementations, at least one of $R_{12}$ to $R_{19}$ may be substituted substituent other than hydrogen. For example, in Formula 2-4, $R_{14}$ and $R_{17}$ may each independently be a substituted or unsubstituted alkyl group having 1 to 10 carbon atoms.

Formula 2-5, each of $R_{12}$ to $R_{19}$ may be a hydrogen atom. In some implementations, at least one of $R_{12}$ to $R_{19}$ may be substituted substituent other than hydrogen. For example, in Formula 2-5, $R_{14}$ and $R_{17}$ may each independently be a substituted or unsubstituted alkyl group having 1 to 10 carbon atoms.

In Formula 2-6, each of $R_{12}$ to $R_{19}$ may be a hydrogen atom. In some implementations, at least one of $R_{12}$ to $R_{19}$ may be a substituent other than a hydrogen. For example, in Formula 2-6, $R_{14}$ and $R_{17}$ may each independently be a substituted or unsubstituted alkyl group having 1 to 10 carbon atoms.

In Formula 2-6, when $Z_1$ is a direct linkage, a resulting ring including $X_1$ becomes a five-member ring (pentagon). When $Z_1$ is O or S, a resulting ring including $X_1$ becomes a six-member ring (hexagon).

In Formula 2-7, each of $R_{12}$ to $R_{19}$ may be a hydrogen atom. In some implementations, at least one of $R_{12}$ to $R_{19}$ may be substituted substituent other than hydrogen. For example, in Formula 2-7, $R_{14}$ and $R_{17}$ may each independently be a substituted or unsubstituted alkyl group having 1 to 10 carbon atoms.

Formula 2 may be represented by, for example, one of Formulae 2-8 to 2-10 below.

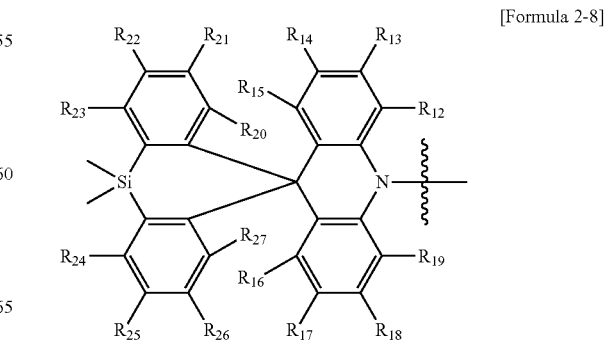

[Formula 2-8]

[Formula 2-9]

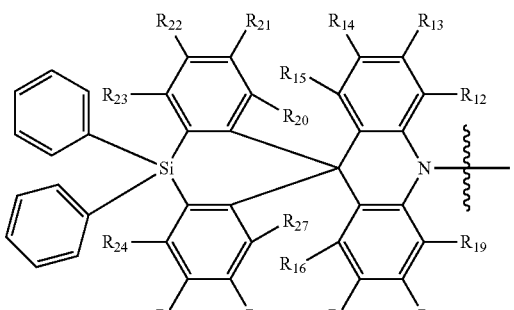

[Formula 2-10]

In Formulae 2-8 to 2-10, $Z_2$ may be a direct linkage, O, or S. The definition of $R_{20}$ to $R_{29}$ may be the same as that of $R_{12}$ to $R_{19}$. $R_{12}$ to $R_{19}$ may be the same as described above.

In Formula 2-8, each of $R_{12}$ to $R_{27}$ may be a hydrogen atom. In some implementations, at least one of $R_{12}$ to $R_{27}$ may be substituent other than hydrogen. For example, in Formula 2-8, $R_{14}$ and $R_{17}$ may each be independently substituted.

In Formula 2-9, each of $R_{12}$ to $R_{27}$ may be a hydrogen atom. In some implementations, at least one of $R_{12}$ to $R_{27}$ may be substituted substituent other than hydrogen. For example, in Formula 2-9, $R_{14}$ and $R_{17}$ may each be independently substituted.

In Formula 2-10, each of $R_{12}$ to $R_{27}$ may be a hydrogen atom. In some implementations, at least one of $R_{12}$ to $R_{27}$ may be substituted substituent other than hydrogen. For example, in Formula 2-10, $R_{14}$ and $R_{17}$ may each be independently substituted.

In Formula 2-10, when $Z_2$ is a direct linkage, a resulting ring including Si becomes a five-member ring (pentagon). When $Z_2$ is O or S, a resulting ring including Si becomes a six-member ring (hexagon).

In the heterocyclic compound according to an embodiment, an absolute value of a difference between a singlet energy level (S1) and a triplet energy level (T1) may be about 0.2 eV or less. When the heterocyclic compound according to an embodiment has a small singlet-triplet energy gap, the heterocyclic compound may be used as an efficient material for thermally activated delayed fluorescence.

In some implementations, the heterocyclic compound represented by Formula 1 according to an embodiment may be, for example, one selected from the compounds represented in Compound Group 1 below.

[Compound Group 1]

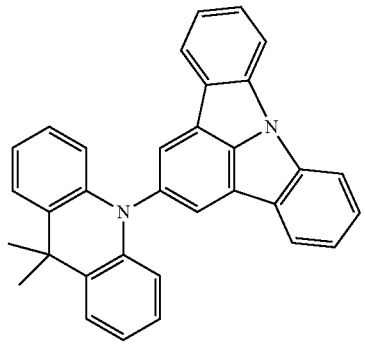

1

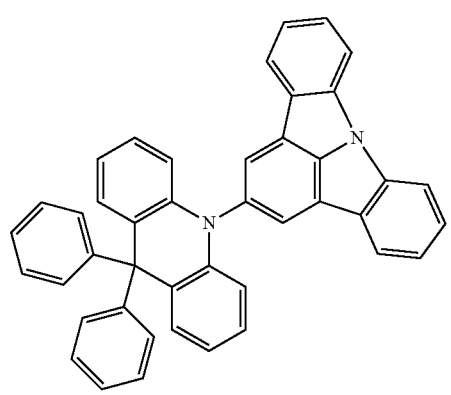

2

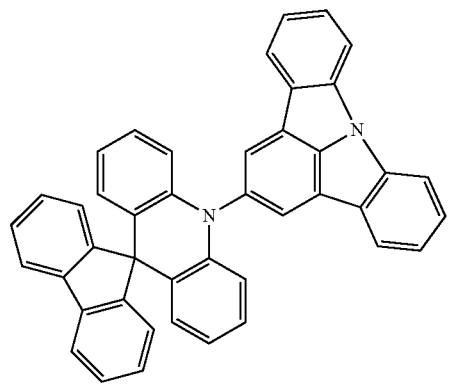

3

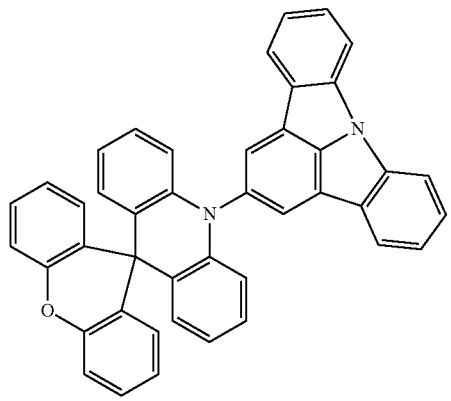

4

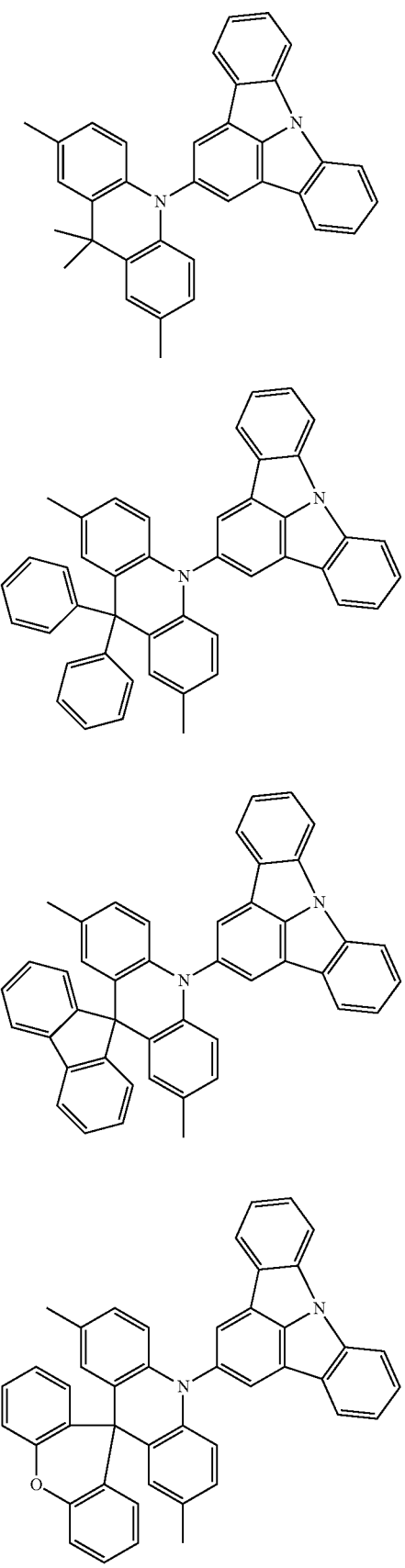
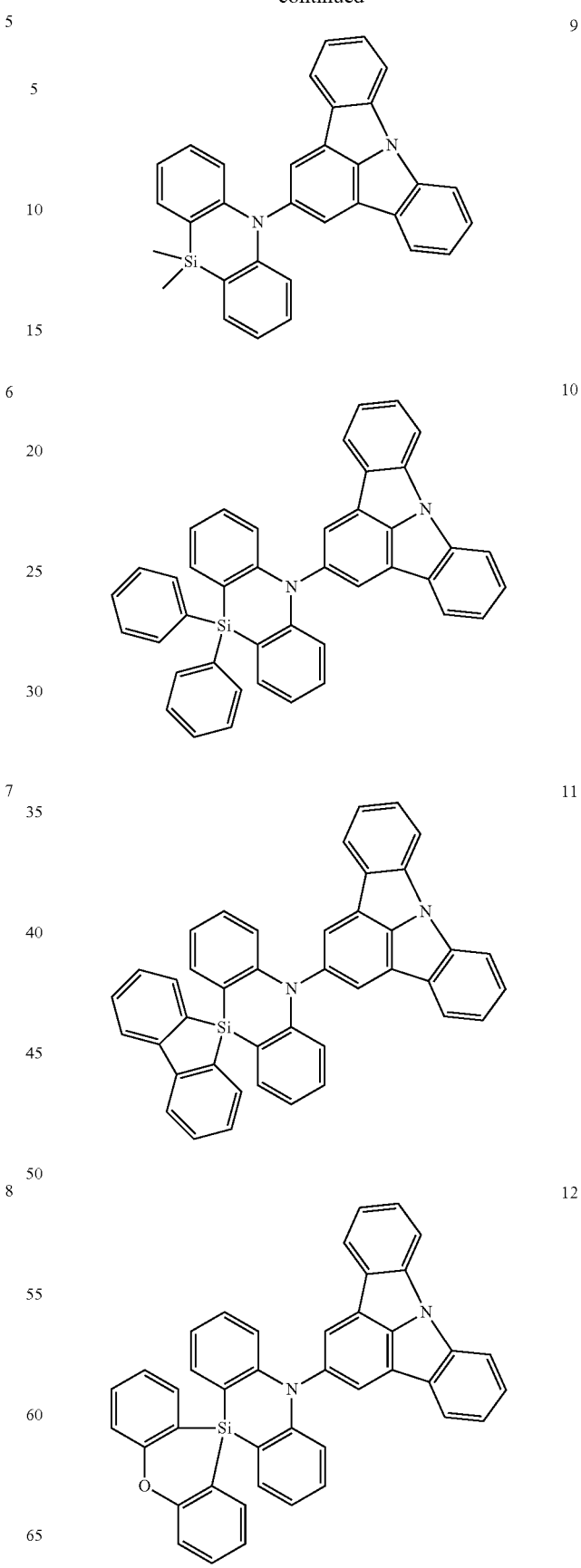

13
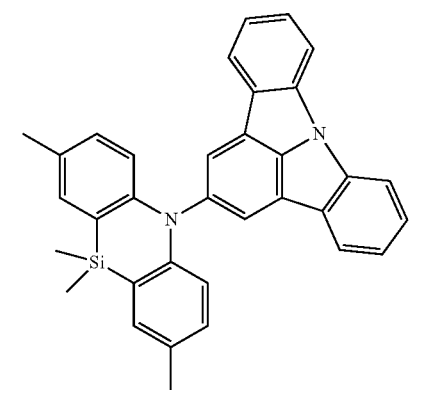
14
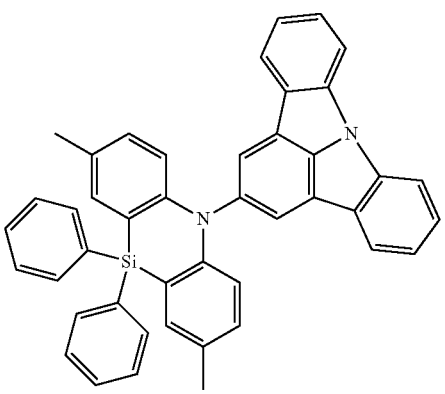
15
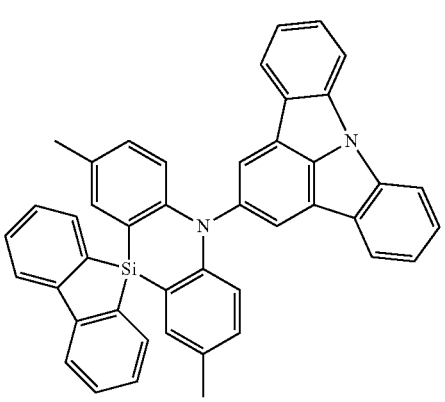
16
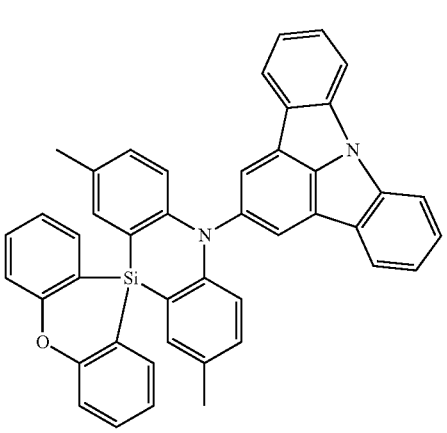
17
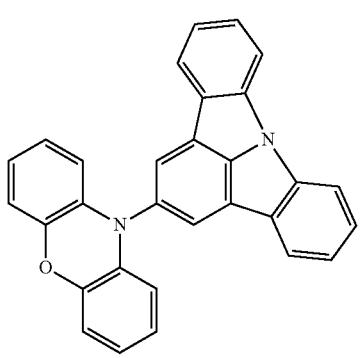
18
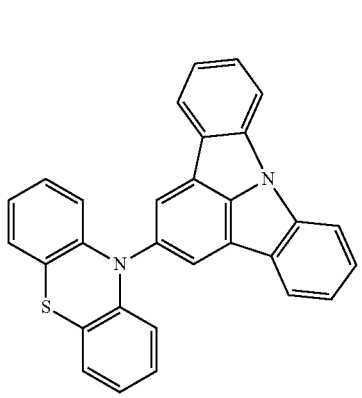
19
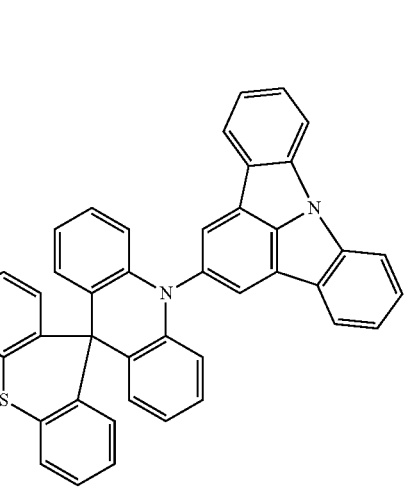
20
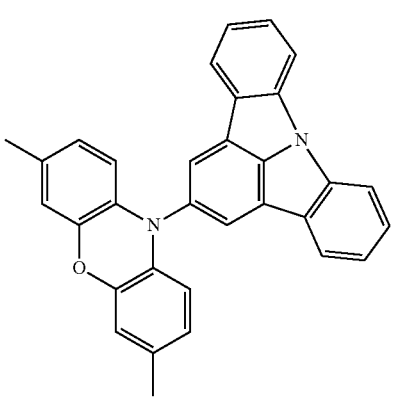

21
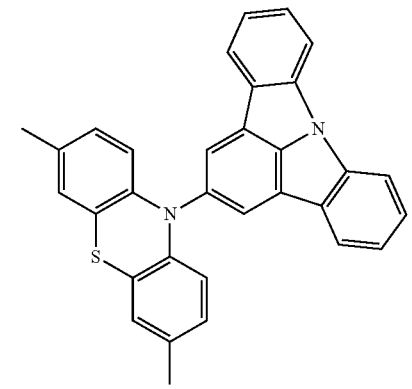
22
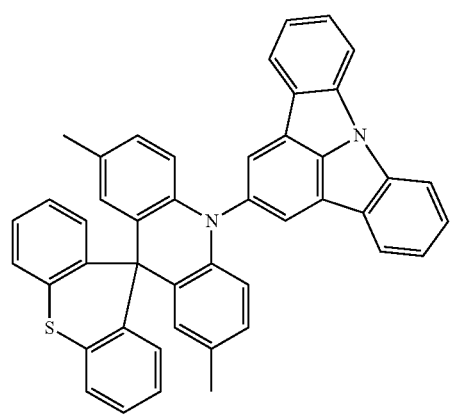
23
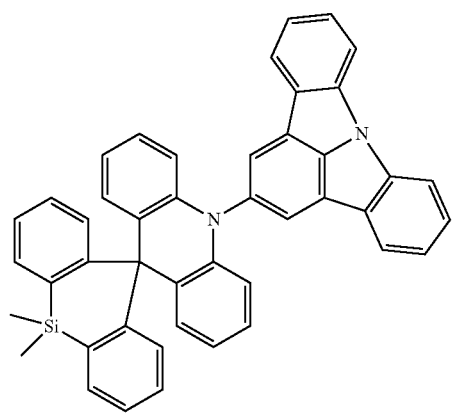
24
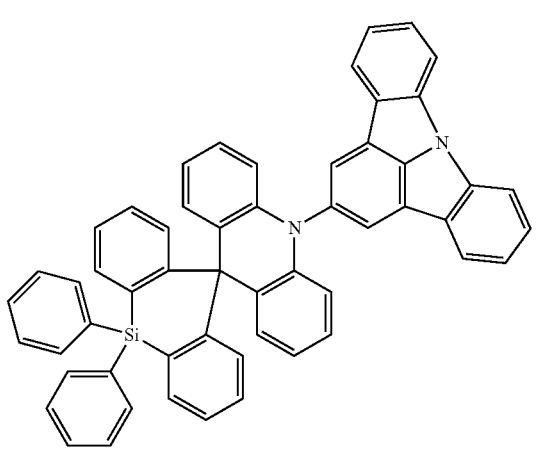
25
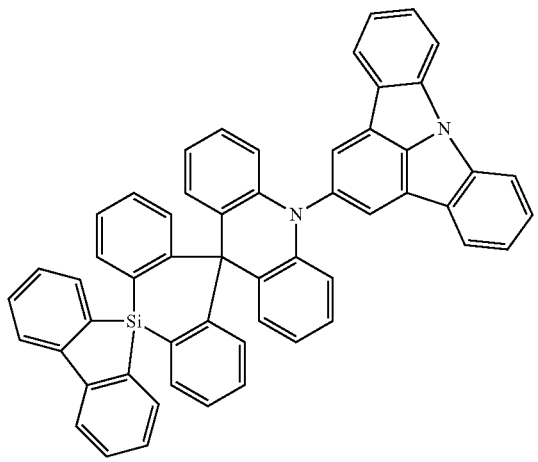
26
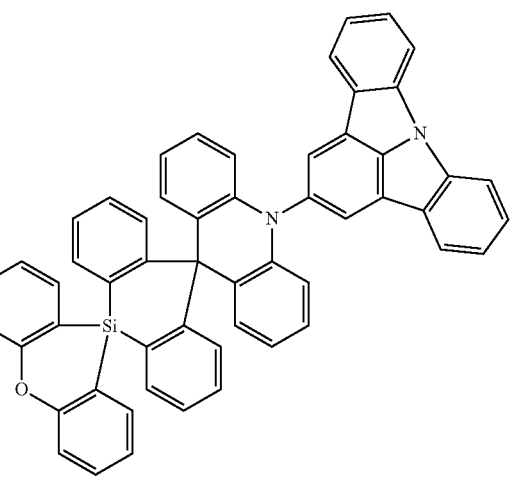
27
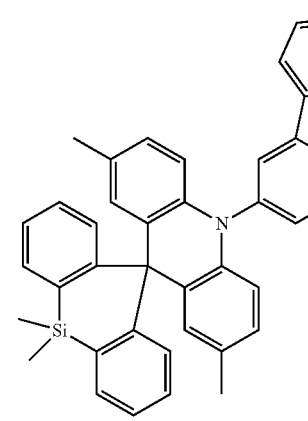

28
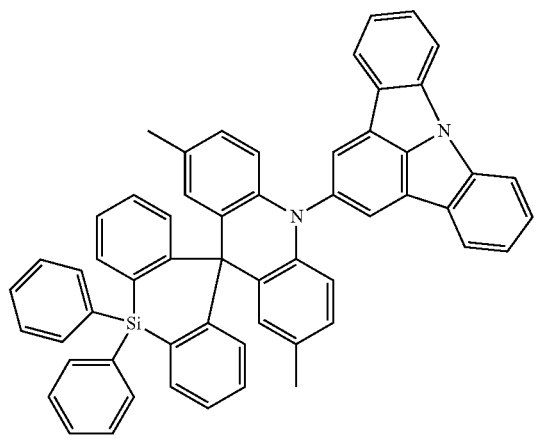
29
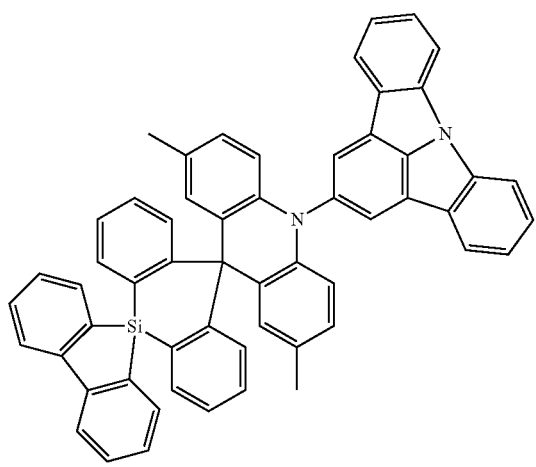
30
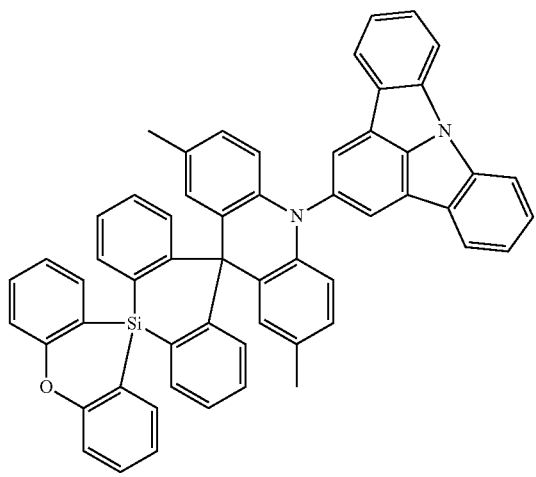
[Compound Group 2]
31
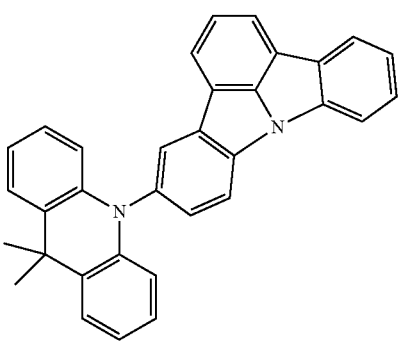
32
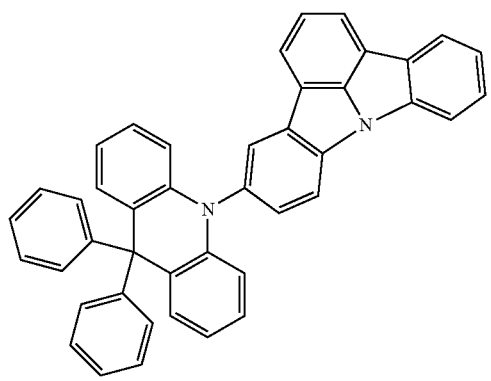
33
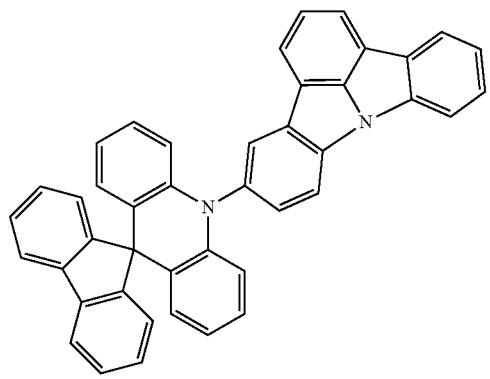
34
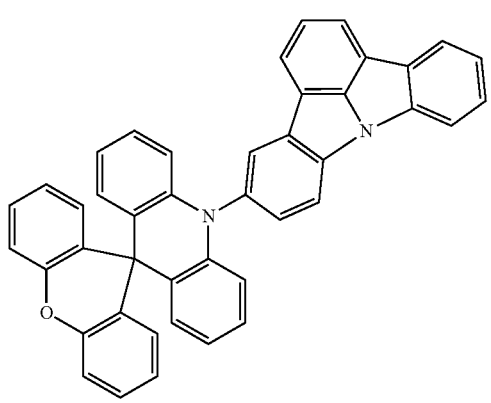
In some implementations, the heterocyclic compound represented by Formula 1 according to an embodiment may be one selected from the compounds represented in Compound Group 2 below.

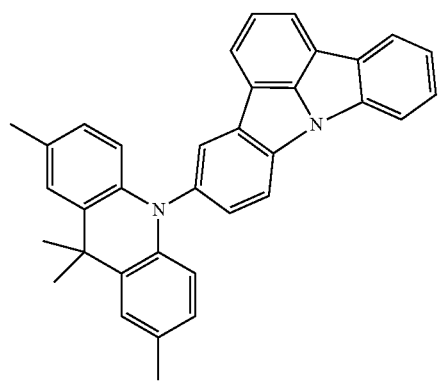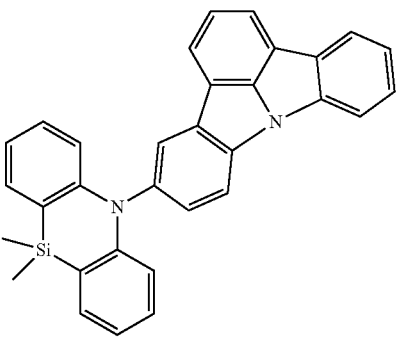

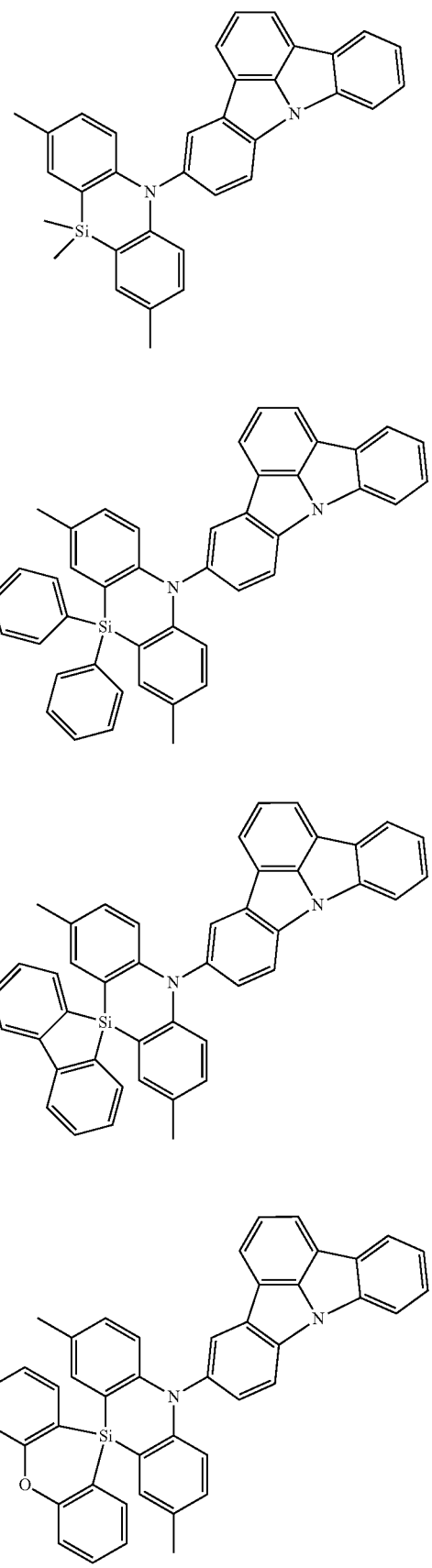
In some implementations, the heterocyclic compound represented by Formula 1 according to an embodiment may be one selected from the compounds represented in Compound Group 3 below.
[Compound Group 3]
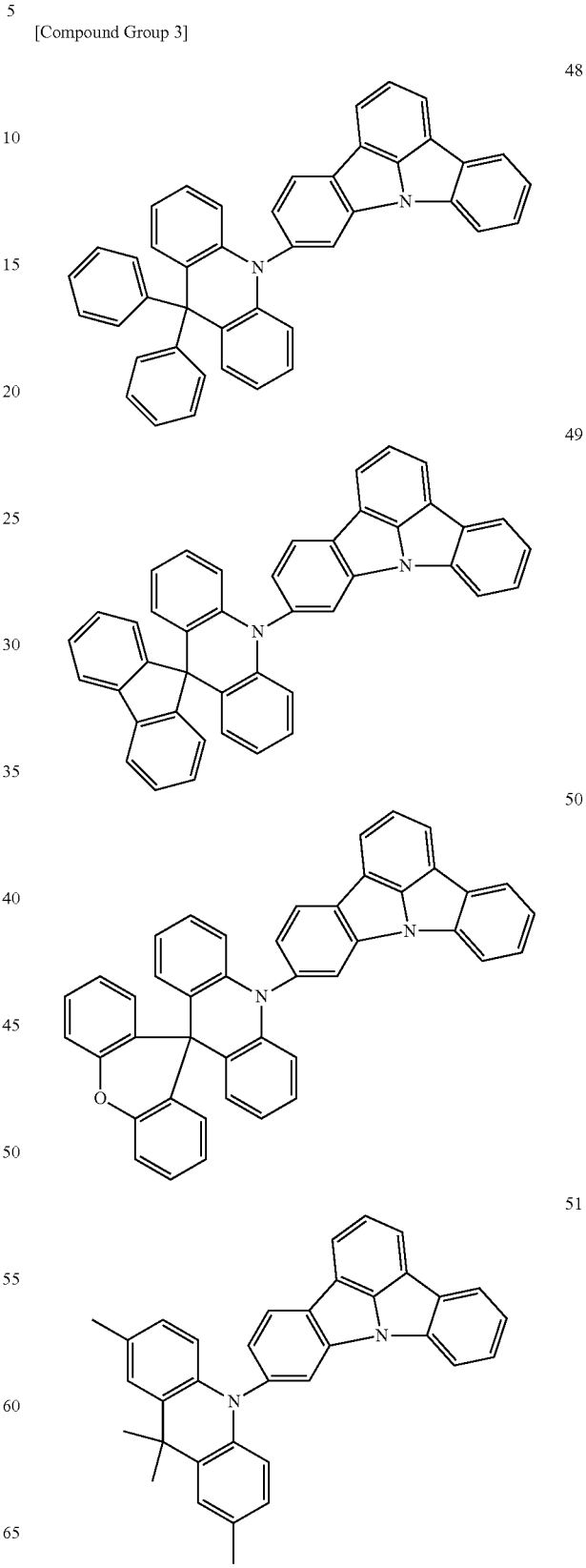

-continued
52
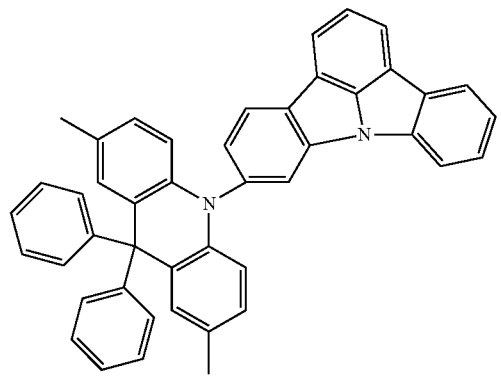
53
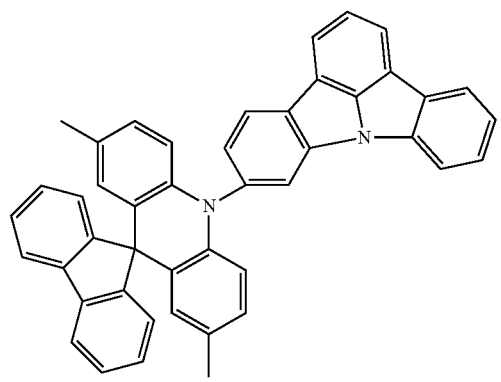
54
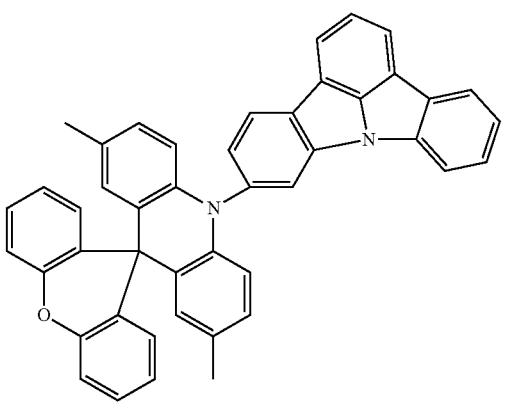
55
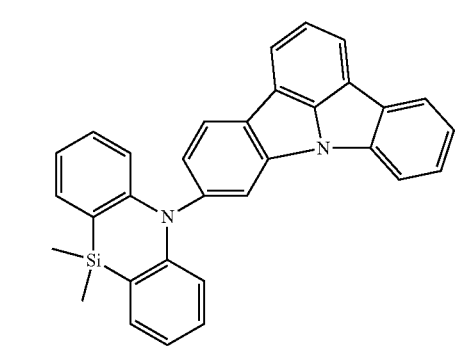
-continued
56
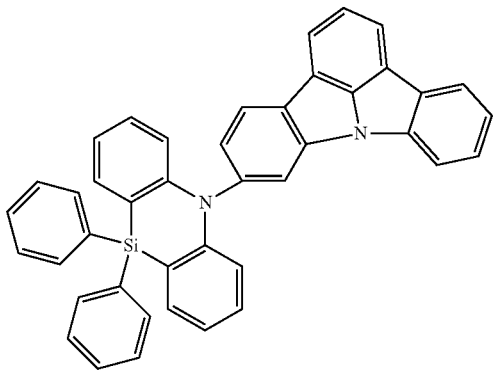
57
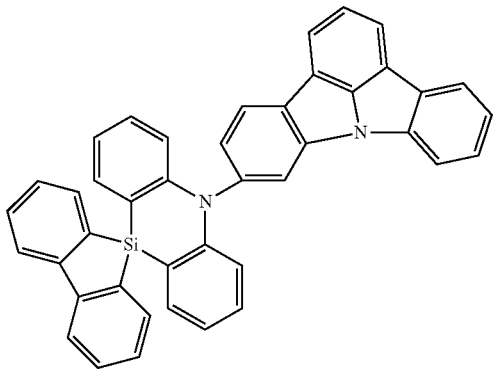
58
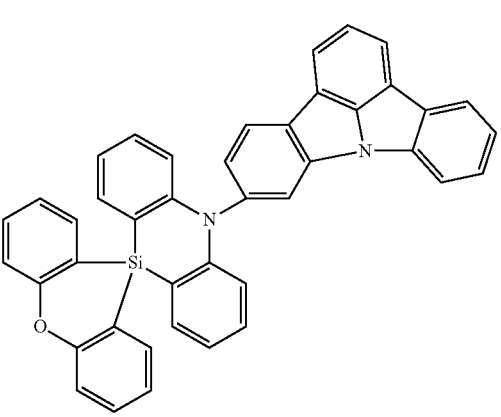
59
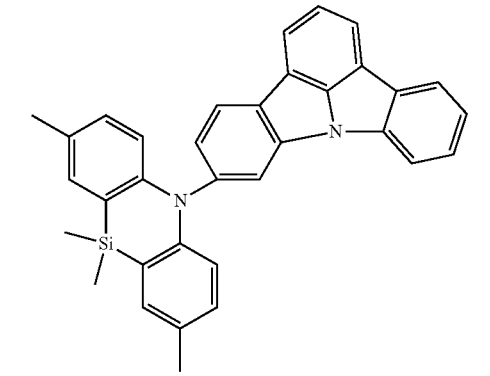

-continued

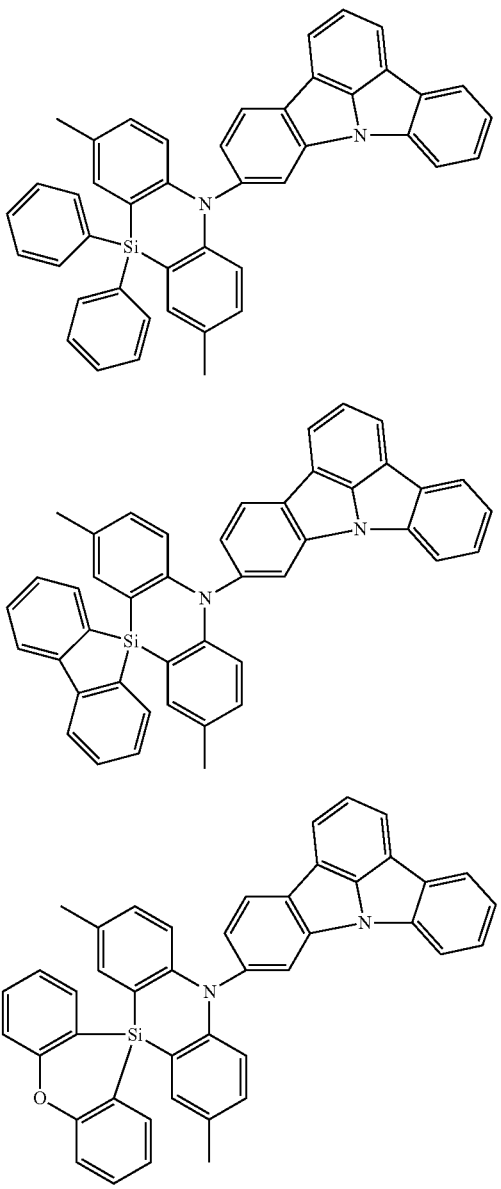

60

61

62

The heterocyclic compound according to an embodiment may be used as a luminescent material of an organic electroluminescence device. For example, the heterocyclic compound may be used as a material for thermally activated delayed fluorescence. The heterocyclic compound according to an embodiment may accomplish blue emission, or, for example, deep blue emission, with high efficiency.

Hereinafter, an organic electroluminescence device according to an embodiment will be explained. The explanation will mainly relate to different aspects of the heterocyclic compound according to embodiments. Aspects that are not explained below may be understood with reference to description of the heterocyclic compound according to embodiment as provided above.

The organic electroluminescence device according to an embodiment may include the above-described heterocyclic compound according to an embodiment.

Figure 2:
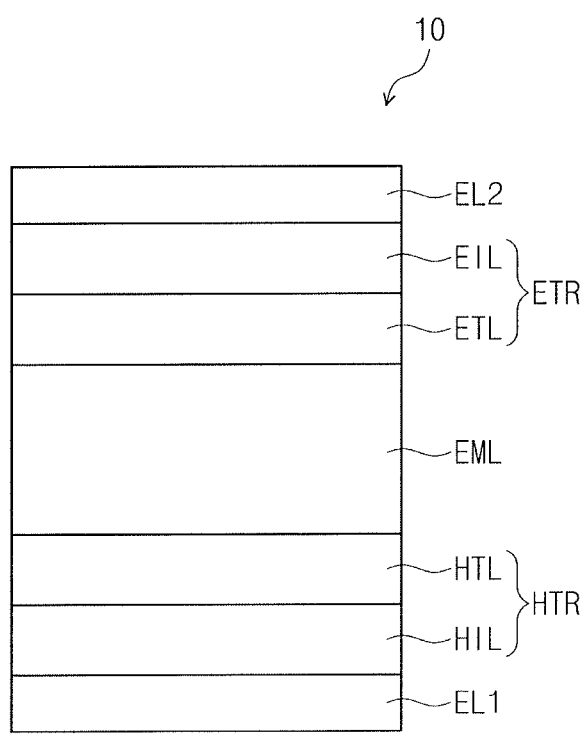
FIG. 2 illustrates a cross-sectional view schematically illustrating the organic electroluminescence device according to an embodiment.

FIG. 1 illustrates a cross-sectional view schematically depicting an organic electroluminescence device according to an embodiment. FIG. 2 illustrates a cross-sectional view schematically depicting an organic electroluminescence device according to an embodiment.

Referring to FIG. 1, an organic electroluminescence device 10 according to an embodiment may include a first electrode EL1, a hole transport region HTR, an emission layer EML, an electron transport region ETR, and a second electrode EL2. As shown in more detail in FIG. 2, the hole transport region HTR of the organic electroluminescence device 10 according to an embodiment may include a hole injection layer HIL and a hole transport layer HTL, and the electron transport region may include an electron transport layer ETL and an electron injection layer EIL. The first electrode EL1 has conductivity. The first electrode EL1 may be a pixel electrode or an anode. The first electrode EL1 may be a transmissive electrode, a transflective electrode, or a reflective electrode. In the case where the first electrode EL1 is the transmissive electrode, the first electrode EL1 may be formed using a transparent metal oxide such as indium tin oxide (ITO), indium zinc oxide (IZO), zinc oxide (ZnO), or indium tin zinc oxide (ITZO). In the case where the first electrode EL1 is the transflective electrode or reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). The first electrode EL1 may include a plurality of layers including the reflective layer or transflective layer formed using the above materials, or a transparent layer formed using ITO, IZO, ZnO, or ITZO.

The hole transport region HTR may be provided on the first electrode EL1. The hole transport region HTR may include at least one of a hole injection layer HIL, a hole transport layer HTL, a hole buffer layer, or an electron blocking layer. The thickness of the hole transport region HTR may be, for example, from about 100 nm to about 150 nm.

The hole transport region HTR may be in a form of a single layer made of a single material, a single layer formed using a plurality of different materials, or a multilayer structure including a plurality of layers formed using a plurality of different materials.

For example, the hole transport region HTR may have the structure of a single layer such as a hole injection layer HIL or a hole transport layer HTL, or may have a structure of a single layer formed using a hole injection material and a hole transport material. In addition, the hole transport region HTR may have a structure of a single layer formed using a plurality of different materials, or a structure laminated one by one from the first electrode EL1 of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/ electron blocking layer, as examples.

The hole transport region HTR may be formed using a suitable method such as a vacuum deposition method, a spin coating method, a cast method, a Langmuir-Blodgett (LB) method, an inkjet printing method, a laser printing method, or a laser induced thermal imaging (LITI) method.

The hole injection layer HIL may include, for example, a phthalocyanine compound such as copper phthalocyanine; N,N'-diphenyl-N,N'-bis-[4-(phenyl-m-tolyl-amino)-phenyl]-biphenyl-4,4'-diamine (DNTPD), 4,4',4"-tris(3-methylphenylphenylamino)triphenylamine (m-MTDATA), 4,4',4"-tris(N,N-diphenylamino)triphenylamine (TDATA), 4,4',4"-tris {N-(2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzene-sulfonic acid (PANI/DBSA), polyaniline/camphor sulfonic acid (PANI/CSA), polyaniline/poly(4-styrenesulfonate) (PANI/PSS), N,N'-dinaphthalene-1-yl)-N,N'-diphenyl-benzidine (NPB), triphenylamine-containing polyether ketone (TPAPEK), 4-isopropyl-4'-methyldiphenyliodonium tetrakis(pentafluorophenyl)borate, dipyrazino[2,3-f: 2',3'-h] quinoxaline-2,3,6,7,10,11-hexacarbonitrile (HAT-CN), etc.

The hole transport layer HTL may include, for example, a carbazole derivative such as N-phenyl carbazole and polyvinyl carbazole, a fluorene-based derivative, N,N'-bis(3-methylphenyl)-N,N'-diphenyl-[1,1-biphenyl]-4,4'-diamine (TPD), a triphenylamine-based derivative such as 4,4',4"-tris(N-carbazolyl)triphenylamine (TCTA), N,N'-di(1-naphthalene-1-yl)-N,N'-diphenyl-benzidine (NPB), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), etc.

The thickness of the hole transport region HTR may be from about 10 nm to about 1,000 nm, or, for example, from about 10 nm to about 100 nm. In the case where the hole transport region HTR includes both the hole injection layer HIL and the hole transport layer HTL, the thickness of the hole injection layer HIL may be from about 10 nm to about 1,000 nm, or, for example, from about 10 nm to about 100 nm, and the thickness of the hole transport layer HTL may be from about 3 nm to about 100 nm. When the thicknesses of the hole transport region HTR, the hole injection layer HIL, and the hole transport layer HTL satisfy the above-described ranges, satisfactory hole transport properties may be obtained without a substantial increase of the driving voltage.

The hole transport region HTR may further include a charge generating material other than the above-described materials to improve conductivity. The charge generating material may be dispersed in the hole transport region HTR uniformly or non-uniformly. The charge generating material may be, for example, a p-dopant. The p-dopant may be one of a quinone derivative, a metal oxide, or a cyano group-containing compound, as examples. For example, the p-dopant may include a quinone derivative such as tetracyano-quinodimethane (TCNQ), 2,3,5,6-tetrafluoro-tetracyanoquinodimethane (F4-TCNQ), or a metal oxide such as tungsten oxide, and molybdenum oxide.

As described above, the hole transport region HTR may further include one of the hole buffer layer or the electron blocking layer in addition to the hole injection layer HIL and the hole transport layer HTL. The hole buffer layer may compensate an optical resonance distance according to the wavelength of light emitted from the emission layer EML and may increase light emission efficiency. Materials included in the hole transport region HTR may be used as materials included in the hole buffer layer. The electron blocking layer may prevent electron injection from the electron transport region ETR into the hole transport region HTR.

The emission layer EML may be provided on the hole transport region HTR. The thickness of the emission layer EML may be, for example, from about 10 nm to about 30 nm. The emission layer EML may be in a form of a single layer made from a single material, a single layer formed using a plurality of different materials, or a multilayer structure having a plurality of layers formed using a plurality of different materials.

Hereinafter, an embodiment of including the heterocyclic compound according to an embodiment in the emission layer EML will be explained. The heterocyclic compound according to an embodiment may be included in at least one organic layer provided between the first electrode EL1 and the second electrode EL2. For example, the heterocyclic compound according to an embodiment may be included in the hole transport layer HTL.

The emission layer EML may include the heterocyclic compound according to an embodiment. The emission layer EML may include a heterocyclic compound represented by Formula 1 below.

[Formula 1]

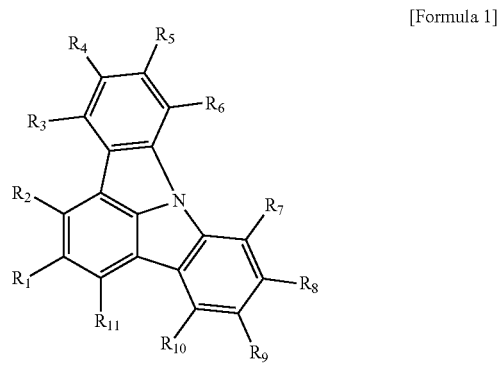

In Formula 1, $R_1$ to $R_{11}$ are the same as described above. For example, at least one of $R_1$ to $R_{11}$ is represented by Formula 2 below.

[Formula 2]

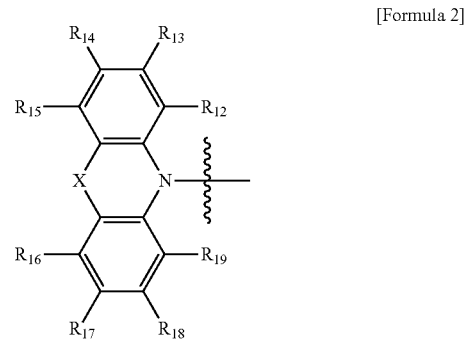

In Formula 2, X, $Y_1$ to $Y_5$, and $R_{12}$ to $R_{19}$ are the same as described above.

The emission layer EML may include one or more kinds of the heterocyclic compounds represented by Formula 1. The emission layer EML may further include a suitable material in addition to the heterocyclic compound represented by Formula 1. For example, the emission layer EML may further include a fluorescent material selected from the group of spiro-DPVBi, 2,2',7,7'-tetrakis(biphenyl-4-yl)-9,9'-spirobifluorene (spiro-6P, spiro-sexiphenyl), distyryl-benzene (DSB), distyryl-arylene (DSA), a polyfluorene (PFO)-based polymer, and a poly(p-phenylene vinylene) (PPV)-based polymer.

The emission layer EML may include the heterocyclic compound according to an embodiment as a luminescent material and may emit thermally activated delayed fluorescence.

The heterocyclic compound according to an embodiment may be a material for thermally activated delayed fluorescence, and may emit blue light. The heterocyclic compound according to an embodiment may emit blue light having a wavelength region less than about 470 nm. For example, the heterocyclic compound may emit blue light having a wavelength region of about 440 nm to about 470 nm, or about 450 nm to about 470 nm.

The heterocyclic compound according to an embodiment may have an absolute value of a difference between a singlet energy level and a triplet energy level of about 0.2 eV or less. By controlling a singlet-triplet energy gap small, thermally activated delayed fluorescence may be efficiently emitted.

The emission layer EML may further include a host. The host may include a suitable host material such as, for example, tris(8-hydroxyquinolino) aluminum (Alq3), 4,4'-bis(N-carbazolyl)-1,1'-biphenyl (CBP), poly(n-vinylcarbazole) (PVK), 9,10-di(naphthalene-2-yl)anthracene (ADN), 4,4',4"-tris(carbazol-9-yl)-triphenylamine (TCTA), 1,3,5-tris(N-phenylbenzimidazole-2-yl)benzene (TPBi), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl) anthracene (MADN), bis[2-(diphenylphosphino)phenyl] ether oxide (DPEPO), hexaphenyl cyclotriphosphazene (CP1), 1,4-bis(triphenylsilyl)benzene (UGH2), hexaphenyl-cyclotrisiloxane (DPSiO3), octaphenylcyclotetra siloxane (DPSiO4), 2,8-bis(diphenylphosphoryl)dibenzofuran (PPF), etc.

The emission layer EML may have a thickness of, for example, about 10 nm to about 100 nm.

The electron transport region ETR may be provided on the emission layer EML. The electron transport region ETR may include at least one of an hole blocking layer, an electron transport layer ETL, or an electron injection layer EIL, as examples.

The electron transport region ETR may be in a form of a single layer made of a single material, a single layer formed using a plurality of different materials, or a multilayer structure including a plurality of layers formed using a plurality of different materials.

For example, the electron transport region ETR may have the structure of a single layer such as an electron injection layer EIL or an electron transport layer ETL, or a single layer structure formed using an electron injection material and an electron transport material. In some implementations, the electron transport region ETR may have a single layer structure formed using a plurality of different materials, or a structure laminated one by one from the emission layer EML of electron transport layer ETL/electron injection layer EIL, or hole blocking layer/electron transport layer ETL/electron injection layer EIL, as examples. The thickness of the electron transport region ETR may be, for example, from about 100 nm to about 150 nm.

The electron transport region ETR may be formed using a suitable method such as a vacuum deposition method, a spin coating method, a cast method, a Langmuir-Blodgett (LB) method, an inkjet printing method, a laser printing method, or a laser induced thermal imaging (LITI) method.

When the electron transport region ETR includes the electron transport layer ETL, the electron transport region ETR may include tris(8-hydroxyquinolinato)aluminum (Alq3), 1,3,5-tri[(3-pyridyl)-phen-3-yl]benzene, 2,4,6-tris (3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)phenyl (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato)aluminum (BAlq), berylliumbis(benzoquinolin-10-olate (Bebq2), 9,10-di(naphthalene-2-yl) anthracene (ADN), or a mixture thereof, as examples. The thickness of the electron transport layer ETL may be from about 10 nm to about 100 nm, or, for example, from about 15 nm to about 50 nm. When the thickness of the electron transport layer ETL satisfies the above-described range, satisfactory electron transport properties may be obtained without the substantial increase of a driving voltage.

When the electron transport region ETR includes the electron injection layer EIL, the electron injection layer EIL may include LiF, lithium quinolate (LiQ), $Li_2O$, BaO, NaCl, CsF, a lanthanide metal such as Yb, or a metal halide such as RbCl and RbI, as examples. The electron injection layer EIL also may be formed using a mixture material of an electron transport material and an insulating organo metal salt. The organo metal salt may be a material having an energy band gap of about 4 eV or more. For example, the organo metal salt may include a metal acetate, a metal benzoate, a metal acetoacetate, a metal acetylacetonate, or a metal stearate. The thickness of the electron injection layer EIL may be from about 0.1 nm to about 10 nm, or, for example, from about 0.3 nm to about 9 nm. When the thickness of the electron injection layer EIL satisfies the above described range, satisfactory electron injection properties may be obtained without inducing a substantial increase of the driving voltage.

The electron transport region ETR may include a hole blocking layer, as described above. The hole blocking layer may include, for example, at least one of 2,9-dimethyl-4,7-diphenyl-1,10-phenanthroline (BCP), or 4,7-diphenyl-1,10-phenanthroline (Bphen).

The second electrode EL2 may be provided on the electron transport region ETR. The second electrode EL2 may be a common electrode or a cathode. The second electrode EL2 may be a transmissive electrode, a transflective electrode or a reflective electrode. When the second electrode EL2 is the transmissive electrode, the second electrode EL2 may include a transparent metal oxide, for example, ITO, IZO, ZnO, ITZO, etc.

When the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound including thereof, or a mixture thereof (for example, a mixture of Ag and Mg). The second electrode EL2 may have a multilayered structure including a reflective layer or a transflective layer formed using the above-described materials or a transparent conductive layer formed using ITO, IZO, ZnO, ITZO, etc.

The second electrode EL2 may be connected with an auxiliary electrode. If the second electrode EL2 is connected with the auxiliary electrode, the resistance of the second electrode EL2 may be decreased.

In the organic electroluminescence device 10, voltages may be applied to each of the first electrode EL1 and the second electrode EL2. Holes injected from the first electrode EL1 may move via the hole transport region HTR to the emission layer EML, and electrons injected from the second electrode EL2 may move via the electron transport region ETR to the emission layer EML. The electrons and holes may be recombined in the emission layer EML to generate excitons, and the excitons may emit light via transition from an excited state to a ground state.

When the organic electroluminescence device 10 is a top emission type, the first electrode EL1 may be a reflective electrode, and the second electrode EL2 may be a transmissive electrode or a transflective electrode. When the organic electroluminescence device 10 is a bottom emission type, the first electrode EL1 may be the transmissive electrode or the transflective electrode, and the second electrode EL2 may be the reflective electrode.

The organic electroluminescence device according to an embodiment includes the heterocyclic compound represented by Formula 1. The organic electroluminescence device may achieve an improvement of efficiency and blue emission (for example, deep blue emission) at the same time.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Synthetic Examples

The heterocyclic compound according to an embodiment may be synthesized as follows, as an example.

1. Synthesis of Compound 3

Compound 3, which is a heterocyclic compound according to an embodiment, may be synthesized, for example, by the following reaction:

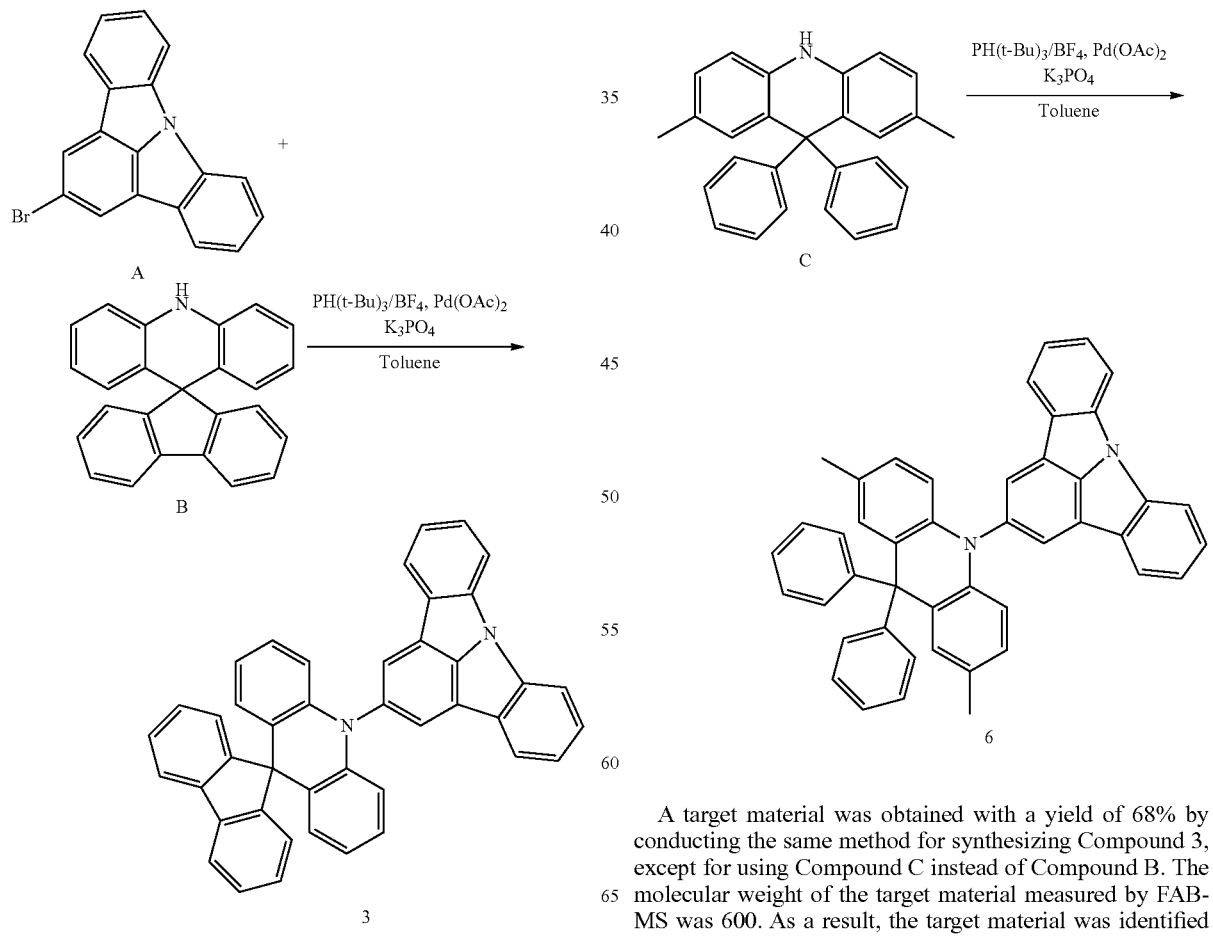

Under an argon (Ar) atmosphere, 2.0 g of Compound A, 2.3 g of Compound B, 0.10 g of palladium acetate, 0.25 g of PH(t-Bu)$_3$/BF$_4$, and 2.7 g of potassium phosphate were added to a 100 ml three neck flask, followed by heating and refluxing in 50 ml of a toluene solvent for about 15 hours. After air cooling, water was added, an organic layer was separated, and solvents were removed. The impurities in the crude product thus obtained was removed by separating using silica gel chromatography (using a mixture solvent of ethyl acetate and hexane), and the product thus obtained was recrystallized with THF to obtain 2.2 g (yield 62%) of a target material as a white solid.

The molecular weight of the target material measured by FAB-MS was 570. As a result, the target material was identified as Compound 3.

2. Synthesis of Compound 6

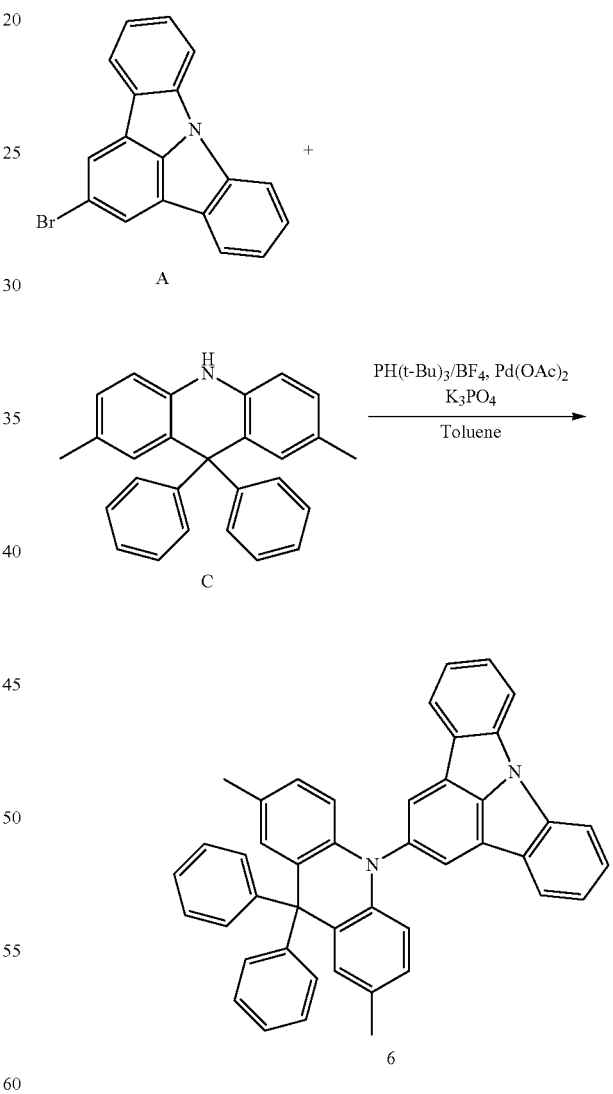

A target material was obtained with a yield of 68% by conducting the same method for synthesizing Compound 3, except for using Compound C instead of Compound B. The molecular weight of the target material measured by FAB-MS was 600. As a result, the target material was identified as Compound 6.

3. Synthesis of Compound 8

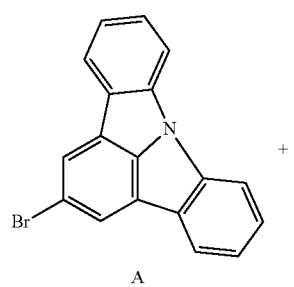
A

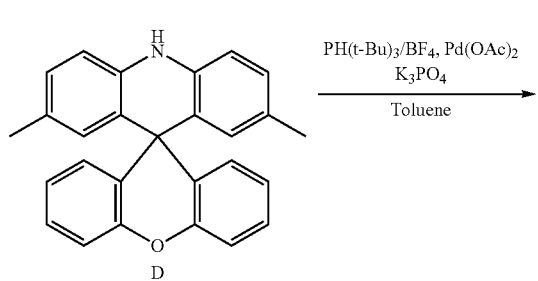
D

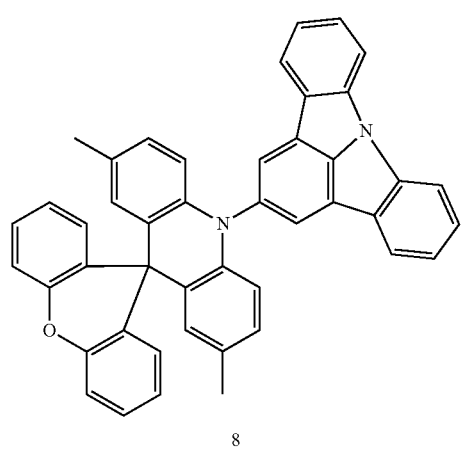
8

A target material was obtained with a yield of 65% by conducting the same method for synthesizing Compound 3, except for using Compound D instead of Compound B. The molecular weight of the target material measured by FAB-MS was 614. As a result, the target material was identified as Compound 8.

4. Synthesis of Compound 14

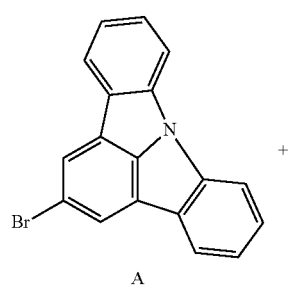
A

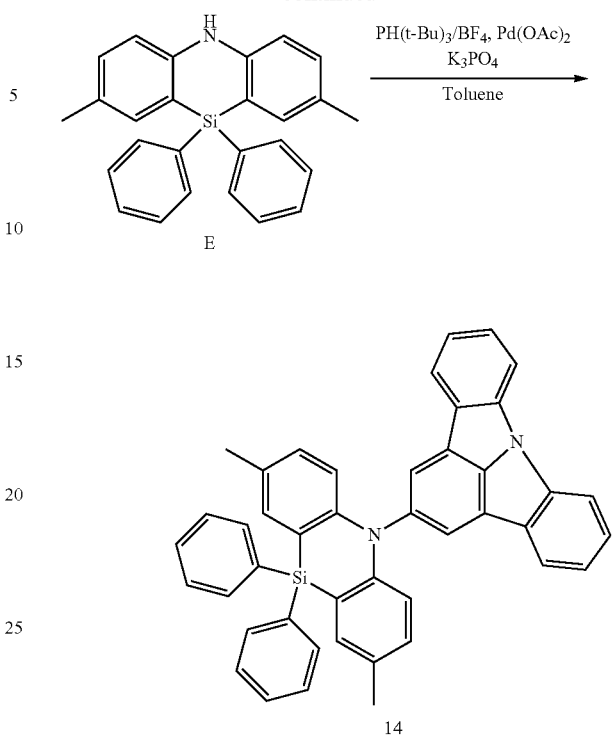
E

14

A target material was obtained with a yield of 72% by conducting the same method for synthesizing Compound 3, except for using Compound E instead of Compound B. The molecular weight of the target material measured by FAB-MS was 616. As a result, the target material was identified as Compound 14.

5. Synthesis of Compound 37

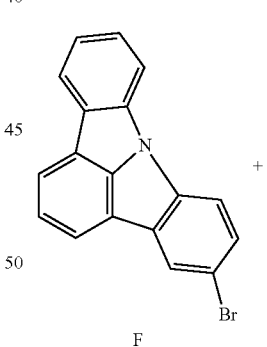
F

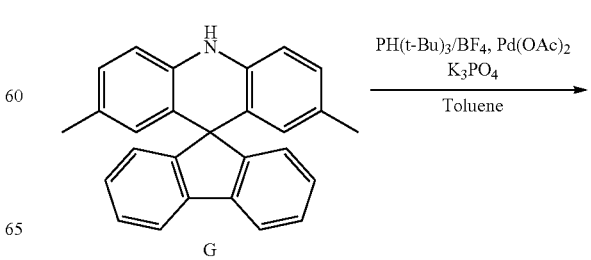
G

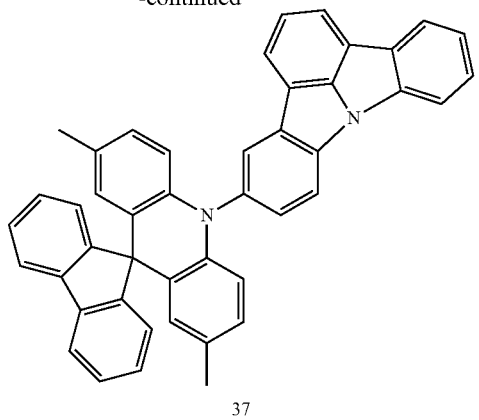

37

A target material was obtained with a yield of 64% by conducting the same method for synthesizing Compound 3, except for using Compound F instead of Compound A and using Compound G instead of Compound B. The molecular weight of the target material measured by FAB-MS was 598. As a result, the target material was identified as Compound 67.

6. Synthesis of Compound 53

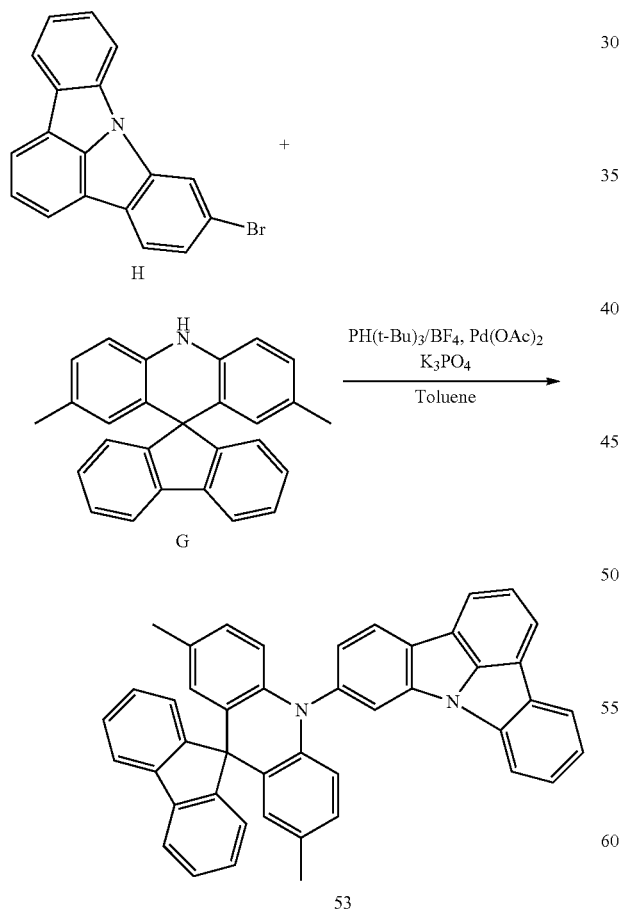

53

A target material was obtained with a yield of 60% by conducting the same method for synthesizing Compound 37, except for using Compound H instead of Compound F. The molecular weight of the target material measured by FAB-MS was 598. As a result, the target material was identified as Compound 53.

Device Manufacturing Examples

Organic electroluminescence devices of Examples 1 to 5 were manufactured using Compounds 3, 6, 8, 14, and 37 as emission layer materials.

Example Compounds

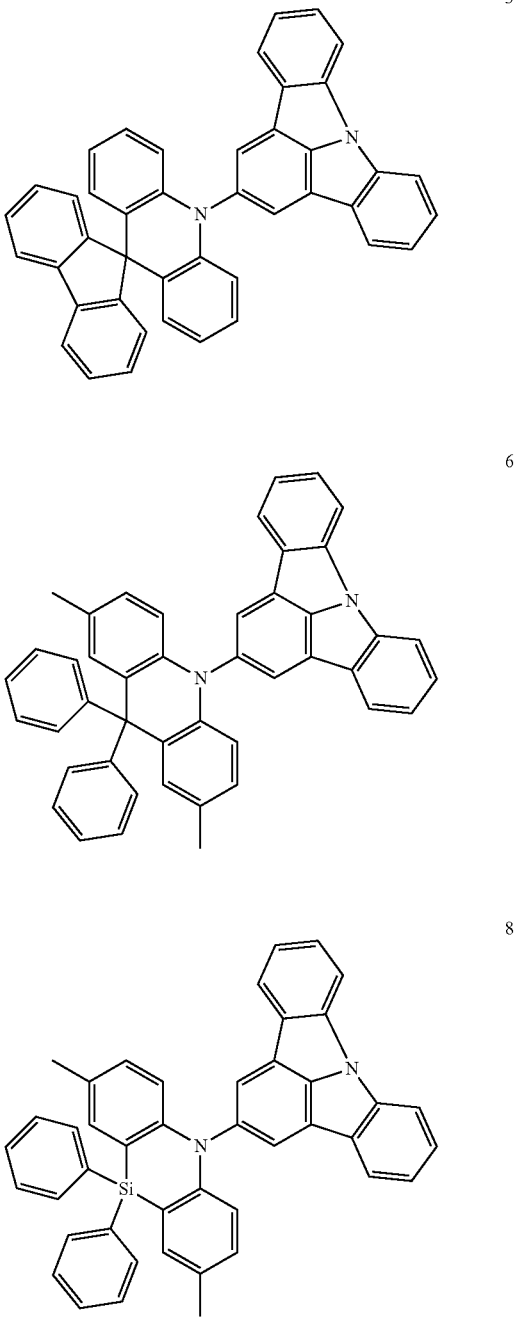

14

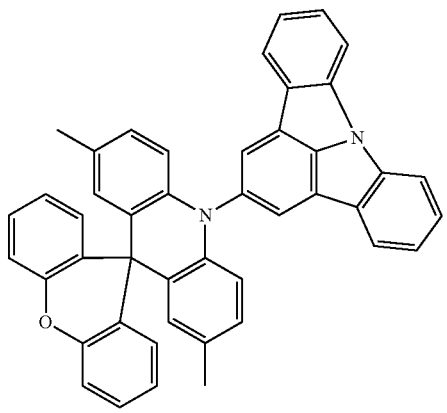

37

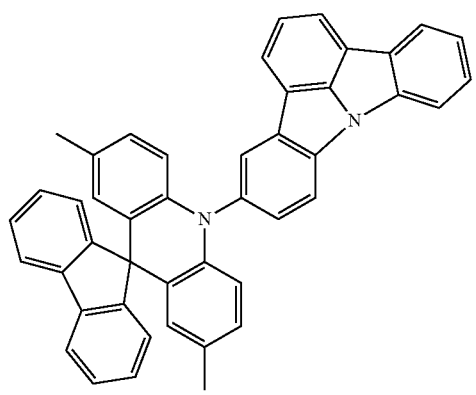

Organic electroluminescence devices of Comparative Examples and 4 were manufactured using Comparative Compounds X-1 to X-4 as emission layer materials.

Comparative Compounds

X-1

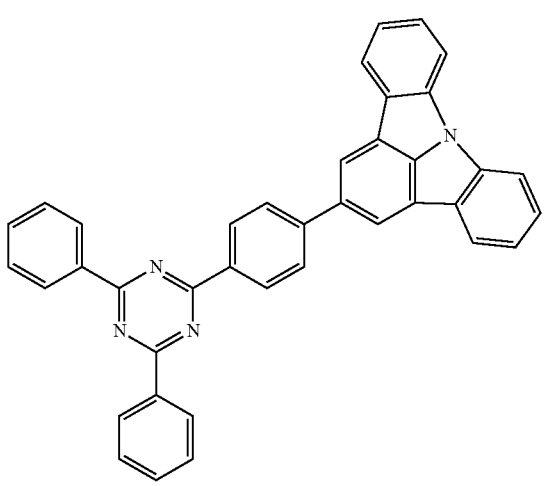

X-2

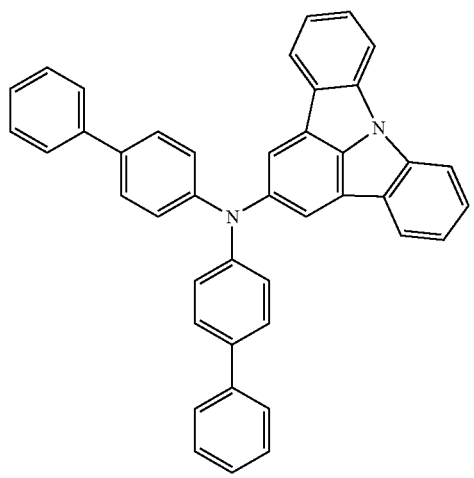

X-3

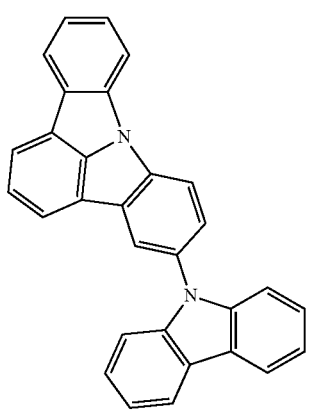

X-4

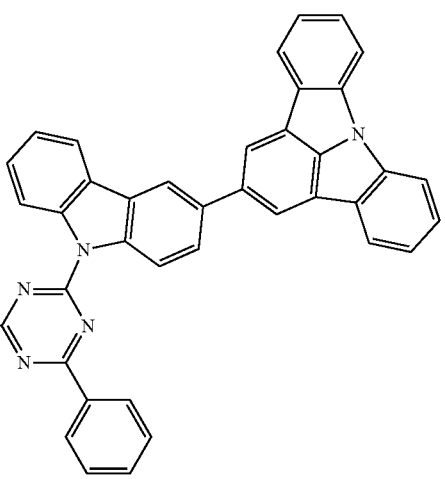

The organic electroluminescence devices of Examples 1 to 5 and Comparative Examples 1 to 4 were manufactured as follows. A first electrode with a thickness of about 150 nm was formed using ITO, a hole injection layer with a thickness of about 10 nm was formed using HAT-CN, a hole transport layer with a thickness of about 80 nm was formed using α-NPD, an electron blocking layer with a thickness of about 5 nm was formed using mCP, an emission layer with a thickness of about 20 nm was formed using bis{2-[di(phenyl) phosphino]phenyl}ether oxide (DPEPO) doped with 18% of the Example Compound or the Comparative Compound, a hole blocking layer with a thickness of about 10 nm was formed using DPEPO, an electron transport layer with a thickness of about 30 nm was formed using TPBi, an electron injection layer with a thickness of about 0.5 nm was formed using LiF, and a second electrode with a thickness of about 100 nm was formed using Al. Each layer was formed by a vacuum deposition method.

TABLE 1

|  | S1 energy level | T1 energy level | $\Delta E_{ST}$ |
|---|---|---|---|
| Example Compound 3 | 2.77 | 2.74 | 0.03 |
| Example Compound 6 | 2.80 | 2.77 | 0.03 |
| Example Compound 8 | 2.81 | 2.77 | 0.04 |
| Example Compound 14 | 2.67 | 2.64 | 0.03 |
| Example Compound 37 | 2.80 | 2.77 | 0.03 |
| Comparative Compound X-1 | 3.37 | 2.76 | 0.61 |
| Comparative Compound X-2 | 2.84 | 2.54 | 0.30 |
| Comparative Compound X-3 | 3.03 | 2.86 | 0.33 |
| Comparative Compound X-4 | 2.77 | 2.42 | 0.35 |

In Table 1, $\Delta E_{ST}$ refers to a difference value between a singlet energy level (A1) and a triplet energy level (T1).

The singlet energy level (S1) and the triplet energy level (T1) were calculated by a non-empirical molecular orbital method. In particular, the calculation was conducted using Gaussian09 manufactured by Gaussian Co., Ltd. and using B3LYP as a functional and 6-31G(d) as a basis function.

Referring to Table 1, all of the Example Compounds showed small values of $\Delta E_{ST}$, and were found to be useful as materials for thermally activated delayed fluorescence. Conversely, the Comparative Compounds showed large values greater than $\Delta E_{ST}$=0.2, and were found to be inadaptable as materials for thermally activated delayed fluorescence.

Then, the maximum emission wavelength ($\lambda_{max}$ (nm)) and external quantum efficiency ($\eta_{ext}$) of the organic electroluminescence devices thus manufactured were measured, and the results are shown in Table 2 below.

The maximum emission wavelength corresponds to the greatest emission wavelength of an emission spectrum at room temperature (about 300K) using a specimen obtained by depositing a compound for measurement on a quartz glass plate. The external quantum efficiency of an organic electroluminescence device including one of the Example Compounds or one of the Comparative Compounds was measured using an external quantum efficiency measurement apparatus of C9920-12 manufactured by HAMAMATSU Photonics Co.

TABLE 2

| Emission layer material | $\lambda$max (nm) | $\eta_{ext}$ |
|---|---|---|
| Example Compound 3 | 448 | 11 |
| Example Compound 6 | 452 | 16 |
| Example Compound 8 | 450 | 17 |
| Example Compound 14 | 453 | 16 |
| Example Compound 37 | 450 | 12 |
| Comparative Compound X-1 | 473 | 4 |
| Comparative Compound X-2 | 460 | 1 |
| Comparative Compound X-3 | 475 | 2 |
| Comparative Compound X-4 | 470 | 1 |

Referring to Table 2, organic electroluminescence devices according to Examples 1 to 5 exhibited shorter wavelength emission and higher efficiency than organic electroluminescence devices according to Comparative Examples 1 to 4. The Example Compounds used in Examples 1 to 5 are the heterocyclic compounds according to exemplary embodiments in which an indolocarbazole unit functions as an electron acceptor, and a unit including nitrogen functions as an electron donor, thereby exhibiting the characteristics as materials for thermally activated delayed fluorescence of an electron acceptor-electron donor type.

In Comparative Example 1, a triazine unit having an electron acceptor capability with respect to an indolocarbazole unit is bonded (Comparative Compound X-1), and the function as the material for thermally activated delayed fluorescence of an electron acceptor-electron donor type was not properly attained. Accordingly, the organic electroluminescence device according to Comparative Example 1 showed low efficiency. In Comparative Example 2, it may be considered that an indolocarbazole unit is an electron acceptor unit, and a bisbiphenylamine unit is an electron donor unit. However, referring to Table 1, the $\Delta E_{ST}$ value is large (about 0.3), and the function as the material for thermally activated delayed fluorescence was not considered to be attained. In addition, each of Comparative Examples 3 and 4 has an electron donating carbazole unit and an electron acceptor-electron donor type, but the $\Delta E_{ST}$ value is large (about 0.3 or more), and the function as the material for thermally activated delayed fluorescence is not considered to be attained.

Further, the emission wavelength of Examples 1 to 5 corresponds to deep blue emission, shorter than the wavelengths of Comparative Examples 1 to 4. The heterocyclic compounds according to embodiments were found to be useful as a material for thermally activated delayed fluorescence, with high efficiency and deep blue emission.

By way of summation and review, an organic electroluminescence device may include, for example, a first electrode, a hole transport layer disposed on the first electrode, an emission layer disposed on the hole transport layer, an electron transport layer disposed on the emission layer, and a second electrode disposed on the electron transport layer is well known. Holes are injected from the first electrode, and the injected holes move via the hole transport layer and are injected into the emission layer. Electrons are injected from the second electrode, and the injected electrons move via the electron transport layer and are injected into the emission layer. The holes and electrons injected into the emission layer recombine to produce excitons in the emission layer. The organic electroluminescence device emits light using light generated by the transition of the excitons to a ground state.

Embodiments provide a heterocyclic compound and an organic electroluminescence device including the same. More particularly, the present disclosure provides a heterocyclic compound for a thermally activated delayed fluorescence material and an organic electroluminescence device including the same in an emission layer.

The heterocyclic compound according to an embodiment may be used as a material for an organic electroluminescence device.

The heterocyclic compound according to an embodiment may be used as a material for emitting delayed fluorescence.

The organic electroluminescence device including the compound according to an embodiment may accomplish blue emission and improved efficiency at the same time.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope thereof as set forth in the following claims.

What is claimed is:

1. A heterocyclic compound represented by the following Formula 1:

[Formula 1]

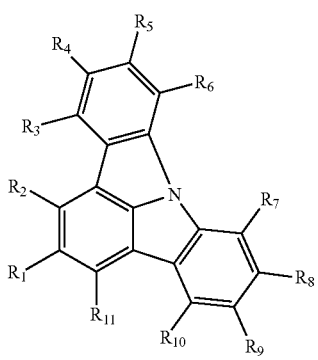

wherein in Formula 1, $R_1$ to $R_{11}$ are each independently a hydrogen atom, a deuterium atom, a substituted or unsubstituted alkyl group having 1 to 10 carbon atoms, a substituted or unsubstituted aryl group having 6 to 30 ring carbon atoms, a substituted or unsubstituted heteroaryl group having 2 to 30 ring carbon atoms, or the following Formula 2, provided that at least one of $R_1$ to $R_{11}$ is represented by the following Formula 2:

[Formula 2]

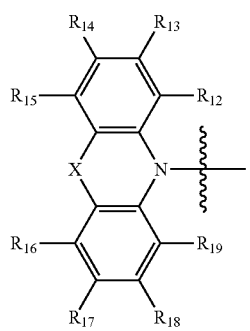

wherein in Formula 2,

represents a bond at one of $R_1$ to $R_{11}$,

X is $CY_1Y_2$, $SiY_3Y_4$, $NY_5$, O or S, $Y_1$ to $Y_5$, and $R_{12}$ to $R_{19}$ are each independently a hydrogen atom, a deuterium atom, a halogen atom, a cyano group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, $Y_1$ and $Y_2$, and $Y_3$ and $Y_4$ may be combined with each other to form a hydrocarbon ring or a heterocycle, and when X is $C(CH_3)_2$, O or S, the $R_{14}$ and $R_{17}$ are each independently methyl, and $R_{12}$, $R_{13}$, $R_{15}$, $R_{16}$, $R_{18}$, and $R_{19}$ are a hydrogen atom, provided that an absolute value of a difference between a singlet energy level and a triplet energy level is about 0.2 eV or less.

2. The heterocyclic compound as claimed in claim 1, wherein Formula 2 is represented by one of the following Formulae 2-1 to 2-3:

[Formula 2-1]

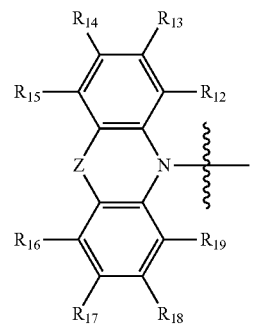

[Formula 2-2]

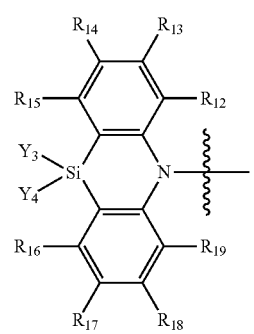

[Formula 2-3]

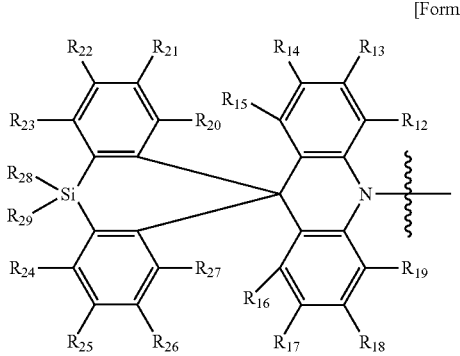

wherein:

in Formula 2-1,

Z is $CY_1Y_2$, $NY_5$, O, or S, $R_{12}$ to $R_{19}$, $Y_1$, $Y_2$ and $Y_5$ are the same as defined in claim 1, when Z is $C(CH_3)_2$, O or S, $R_{14}$ and $R_{17}$ are each independently methyl, and $R_{12}$, $R_{13}$, $R_{15}$, $R_{16}$, $R_{18}$, and $R_{19}$ are a hydrogen atom, in Formula 2-3, the definition of $R_{20}$ to $R_{29}$ is the same as that of $R_{12}$ to $R_{19}$, and $R_{28}$ and $R_{29}$ may be combined with each other to form a hydrocarbon ring or a heterocycle, in Formula 2-2 to Formula 2-3, $R_{12}$ to $R_{19}$, and $Y_1$ to $Y_5$ are the same as defined in claim 1.

3. The heterocyclic compound as claimed in claim 1, wherein one of $R_1$, $R_4$, or $R_5$ is represented by the Formula 2.

4. The heterocyclic compound as claimed in claim 1, wherein Formula 1 is represented by the following Formula 1-1:

[Formula 1-1]

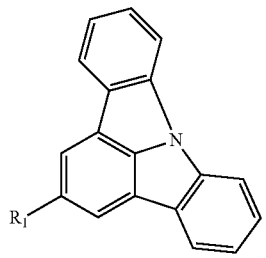

wherein in Formula 1-1, $R_1$ is represented by the Formula 2.

5. The heterocyclic compound as claimed in claim 1, wherein Formula 1 is represented by the following Formula 1-2:

[Formula 1-2]

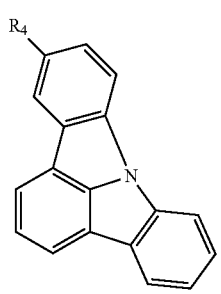

wherein in Formula 1-2, $R_4$ is represented by the Formula 2.

6. The heterocyclic compound as claimed in claim 1, wherein Formula 1 is represented by the following Formula 1-3:

[Formula 1-3]

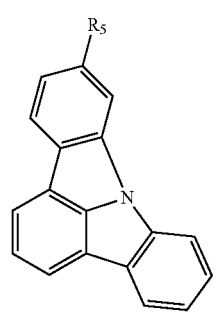

wherein in Formula 1-3, $R_5$ is represented by the Formula 2.

7. The heterocyclic compound as claimed in claim 1, wherein Formula 2 is represented by one of the following Formulae 2-4 to 2-7:

[Formula 2-4]

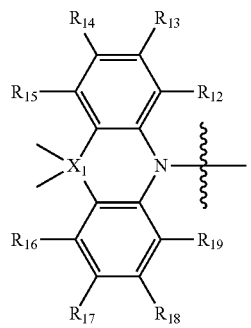

[Formula 2-5]

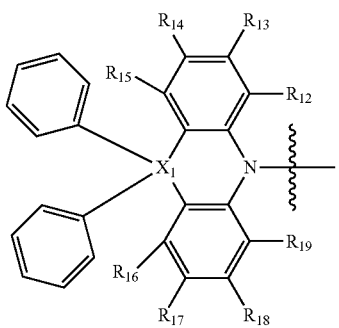

[Formula 2-6]

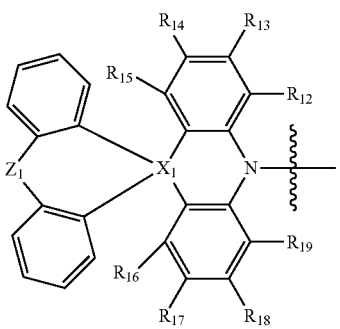

[Formula 2-7]

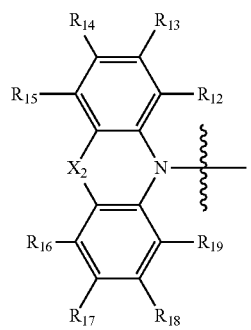

where $X_1$ is C or Si, $X_2$ is O or S, $Z_1$ is a direct linkage, O, or S, $R_{12}$ to $R_{19}$ are the same as defined in claim 1, when $X_1$ is C in Formula 2-4, $R_{14}$ and $R_{17}$ are each independently methyl, and $R_{12}$, $R_{13}$, $R_{15}$, $R_{16}$, $R_{18}$, and $R_1$ are a hydrogen atom, and when $X_2$ is O or S in Formula 2-7, $R_{14}$ and $R_{17}$ are each independently methyl, and $R_{12}$, $R_{13}$, $R_{15}$, $R_{16}$, $R_{18}$, and $R_{19}$ are a hydrogen atom.

8. The heterocyclic compound as claimed in claim 1, wherein Formula 2 is represented by one of the following Formulae 2-8 to 2-10:

[Formula 2-8]

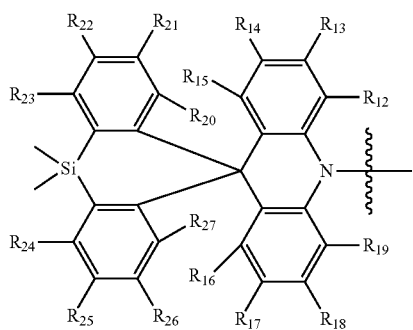

[Formula 2-9]

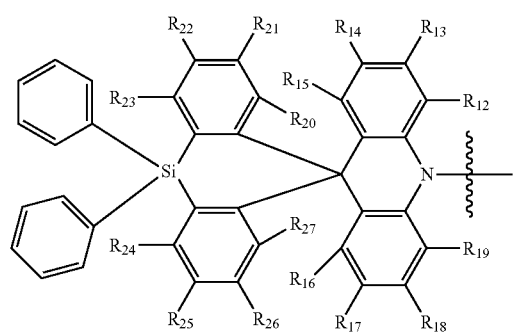

[Formula 2-10]

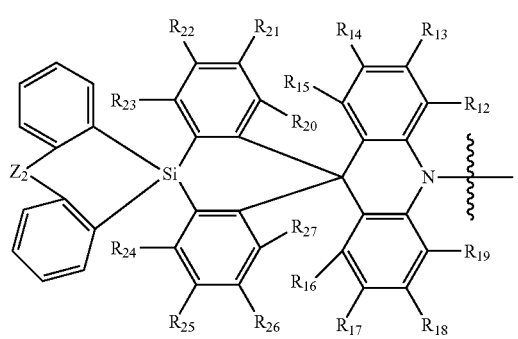

where $Z_2$ is a direct linkage, O, or S, the definition of $R_{20}$ to $R_{29}$ is the same as that of $R_{12}$ to $R_{19}$, and $R_{12}$ to $R_{19}$ are the same as defined in claim 1.

9. The heterocyclic compound as claimed in claim 1, wherein the heterocyclic compound represented by Formula 1 is one selected from compounds represented in the following Compound Group 1:

[Compound Group 1]

2

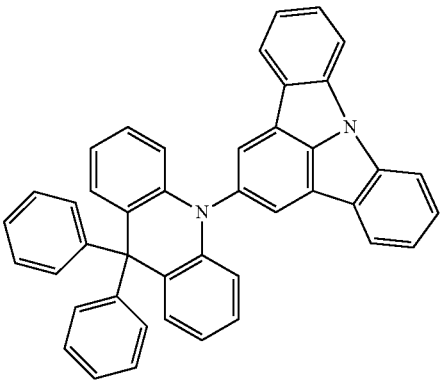

3

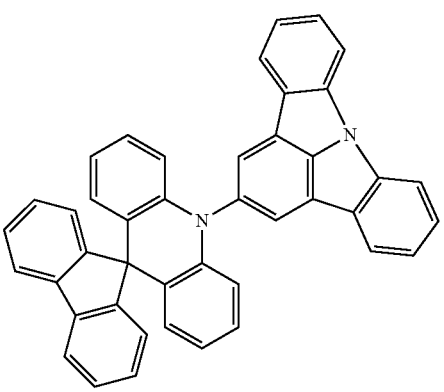

4

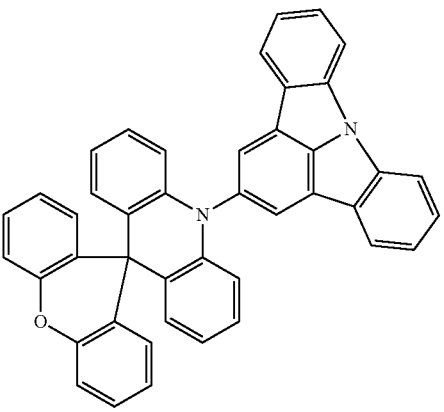

5

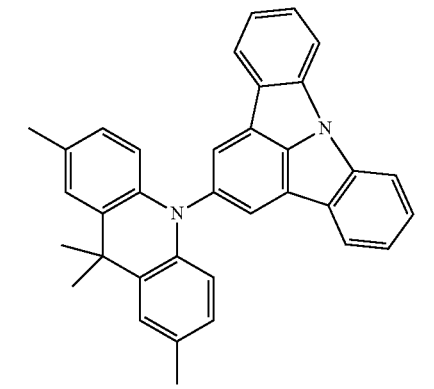

6
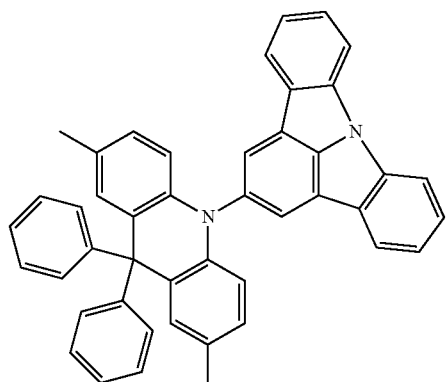
7
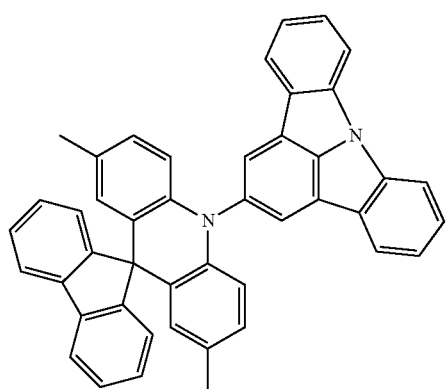
8
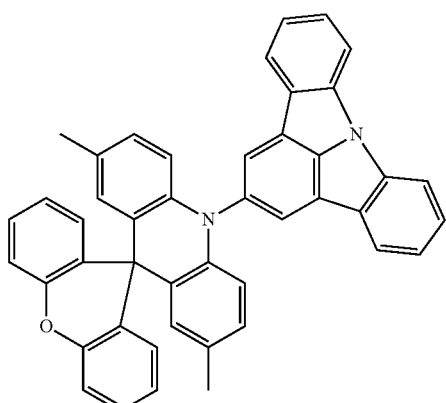
9
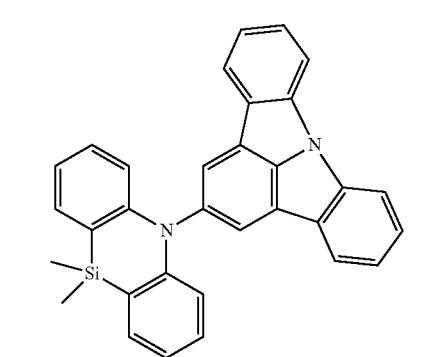
10
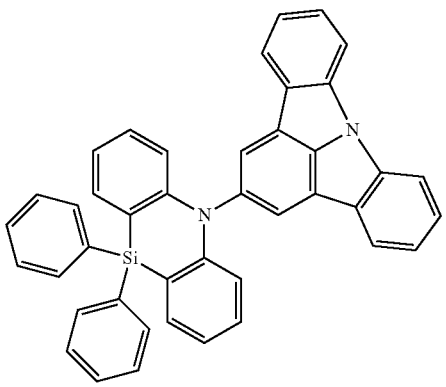
11
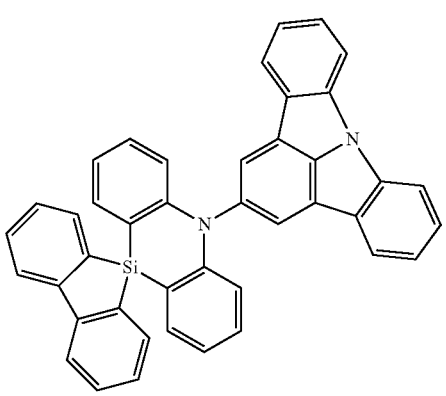
12
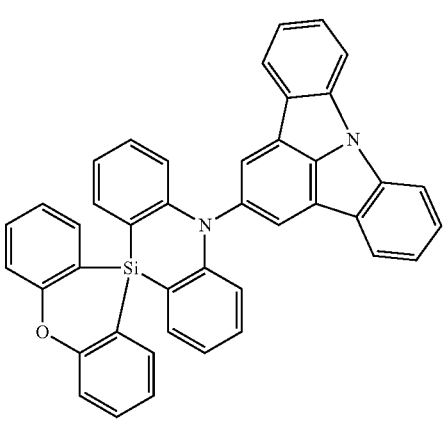
13
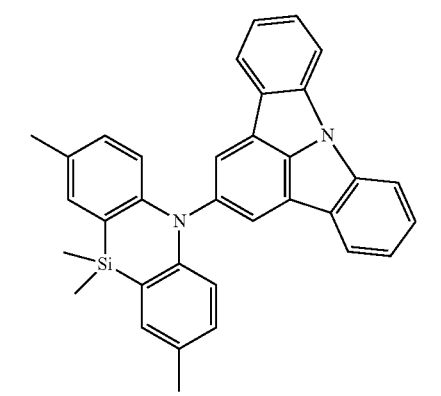

14
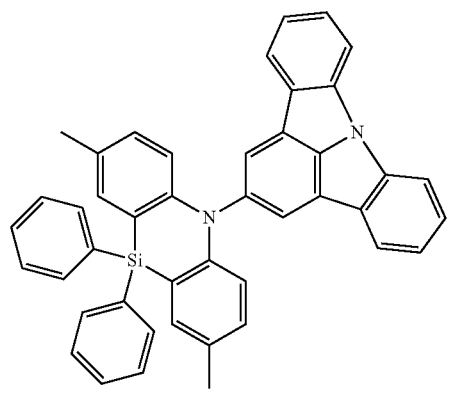
15
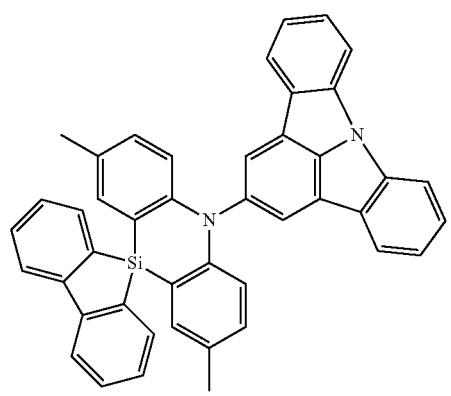
16
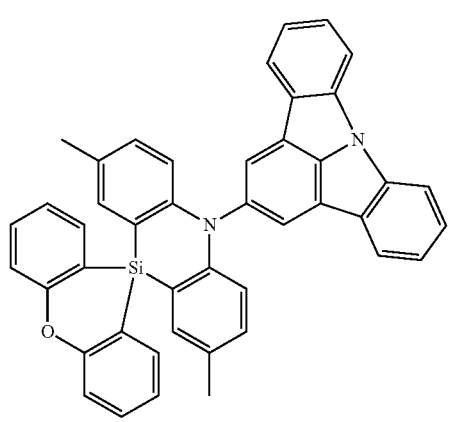
19
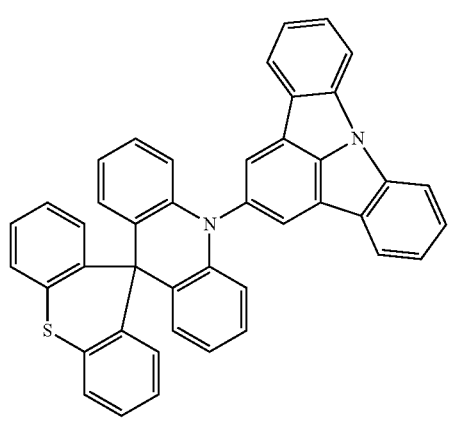
20
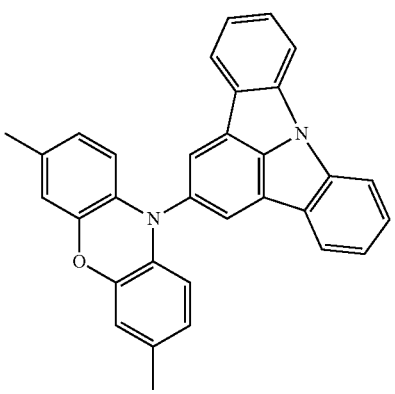
21
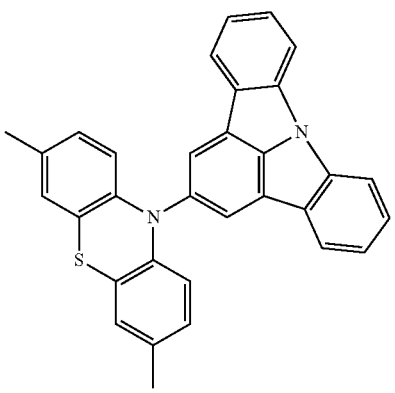
22
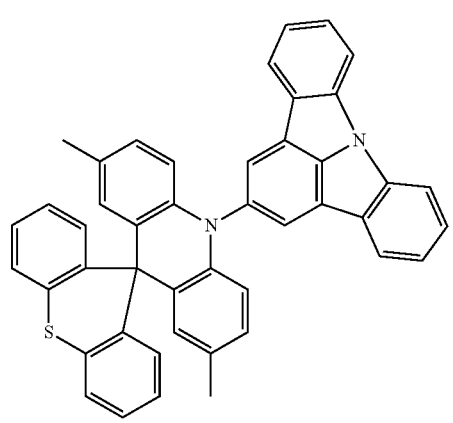
23
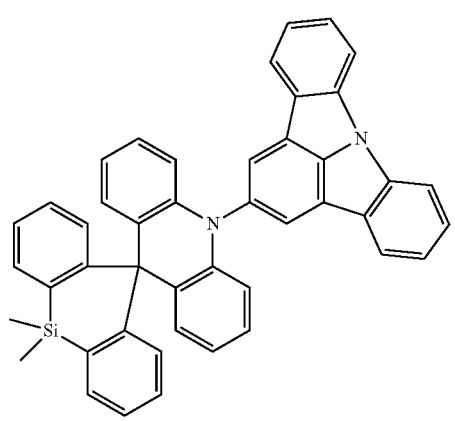

24
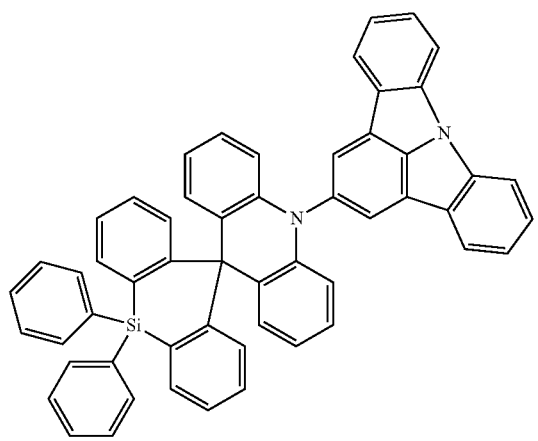
25
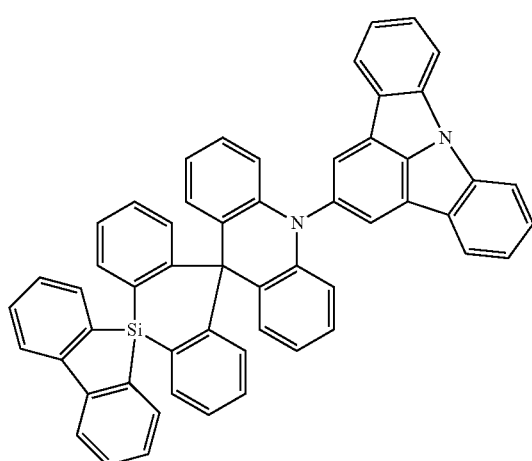
26
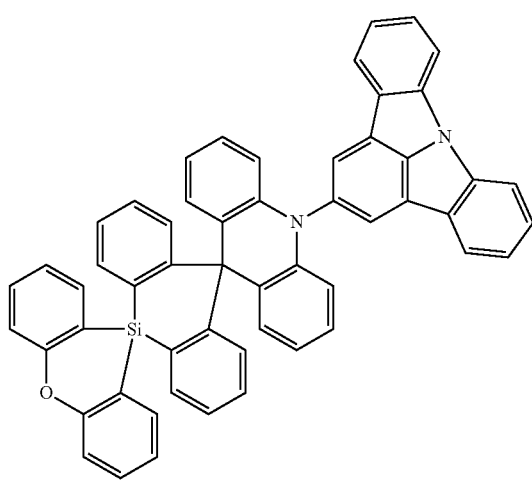
27
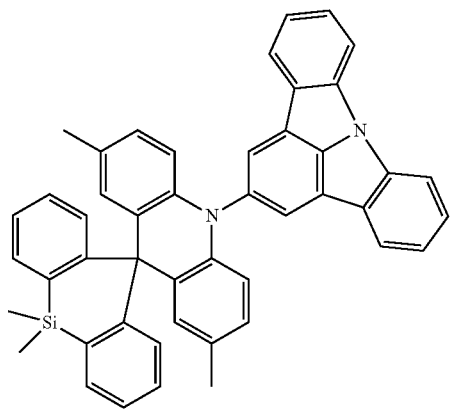
28
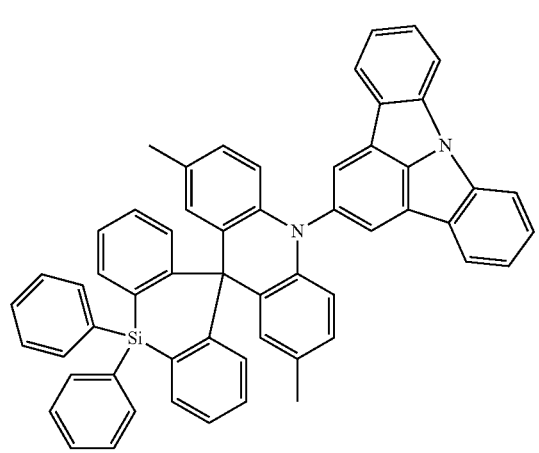
29
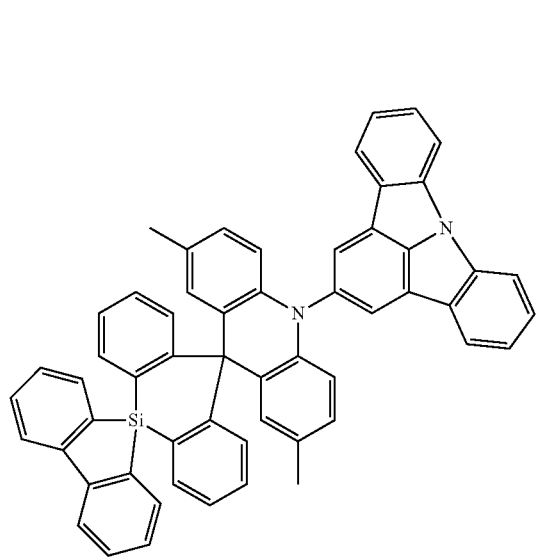

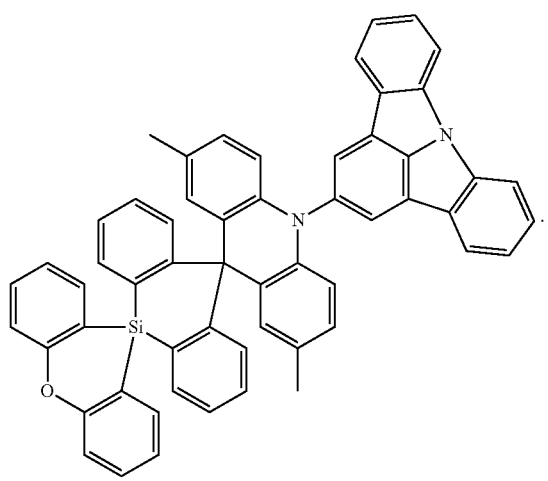
30
10. The heterocyclic compound as claimed in claim 1, wherein the heterocyclic compound represented by Formula 1 is one selected from compounds represented in the following Compound Group 2:
[Compound Group 2]
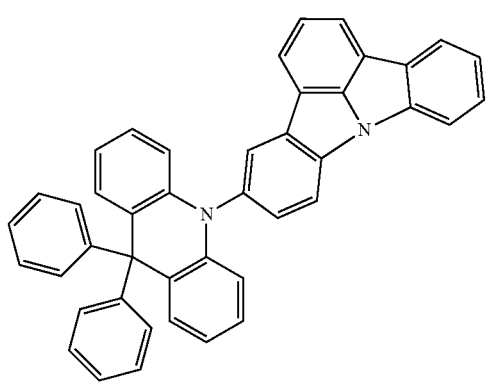
32
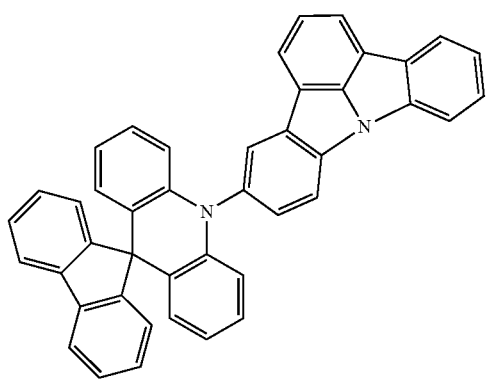
33
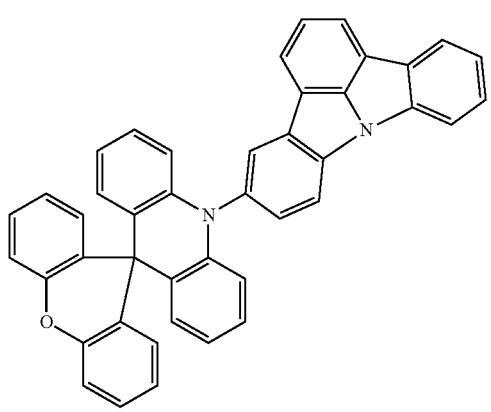
34
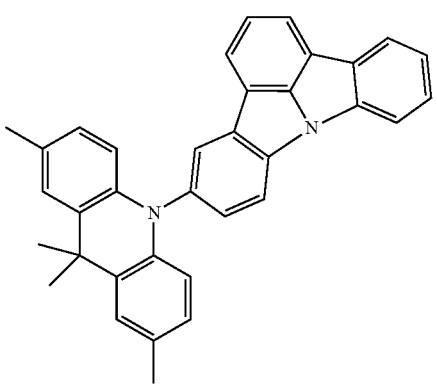
35
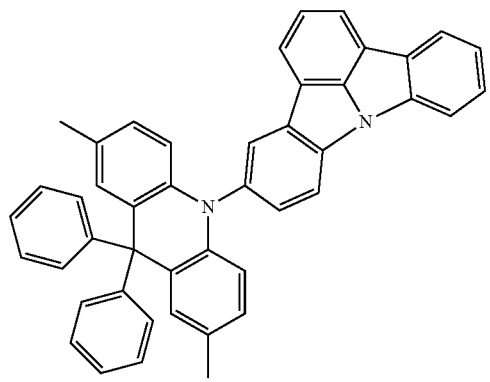
36
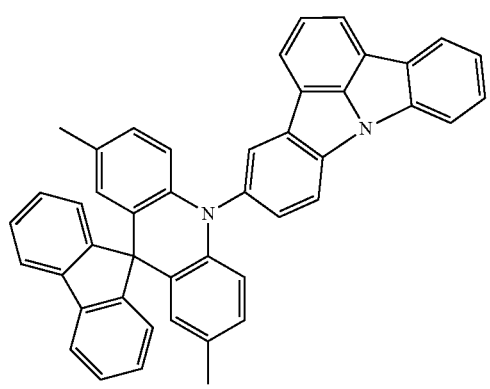
37

38
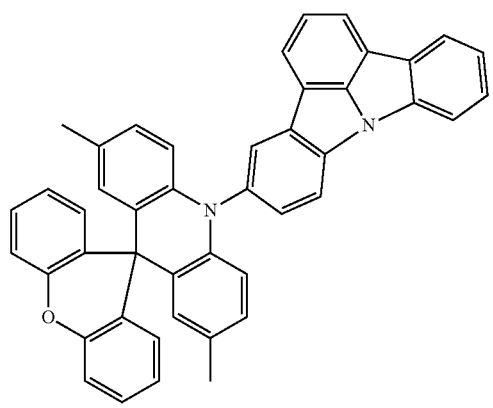
39
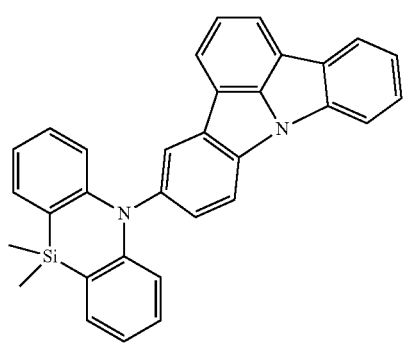
40
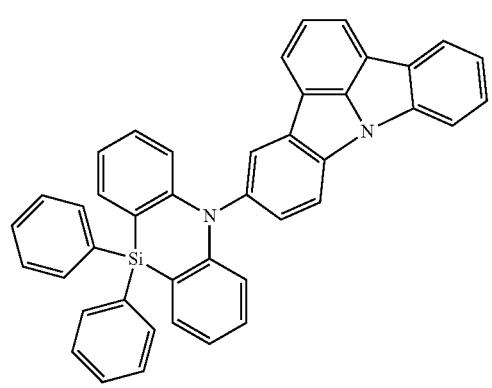
41
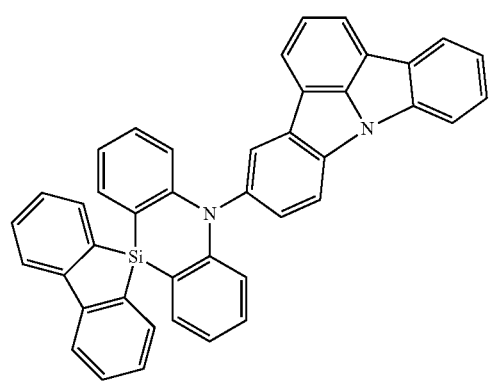
42
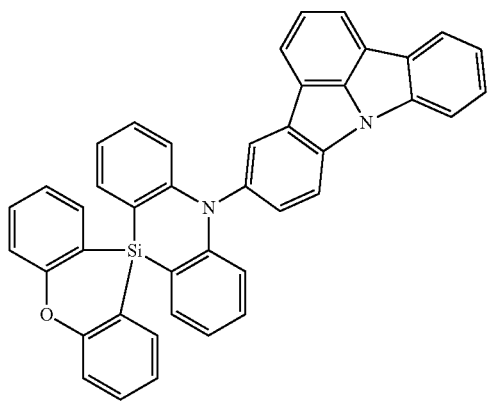
43
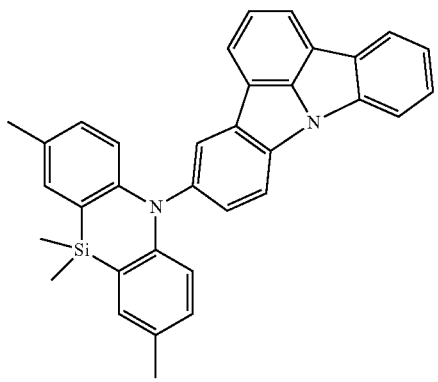
44
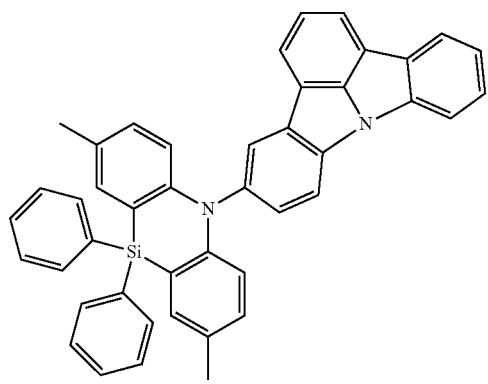
45
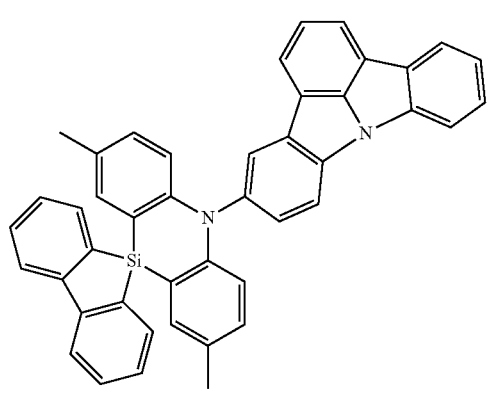

46
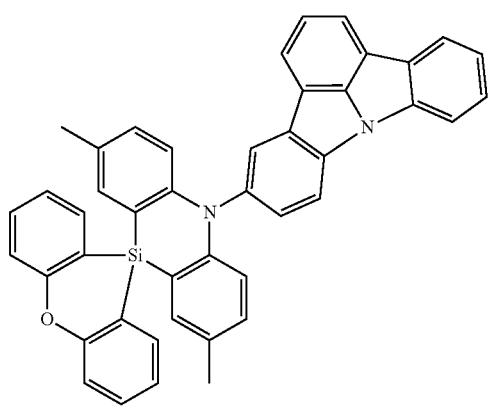
11. The heterocyclic compound as claimed in claim 1, wherein the heterocyclic compound represented by Formula 1 is one selected from compounds represented in the following Compound Group 3:
[Compound Group 3]
48
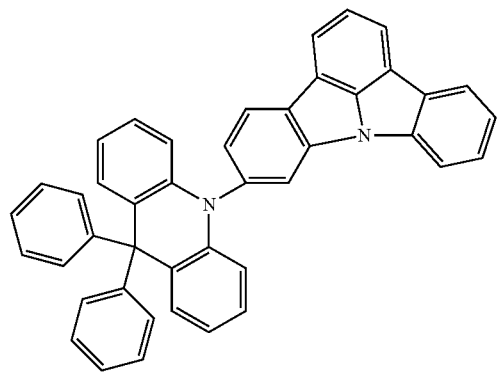
49
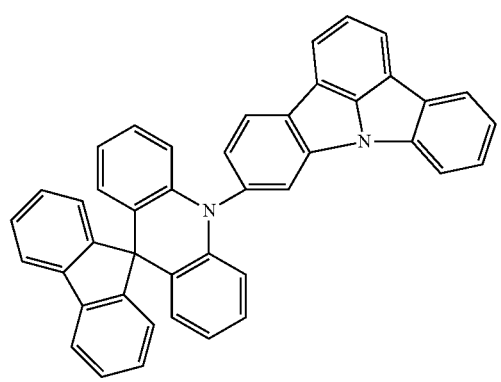
50
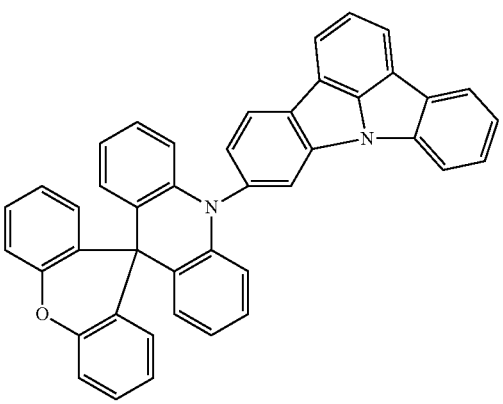
51
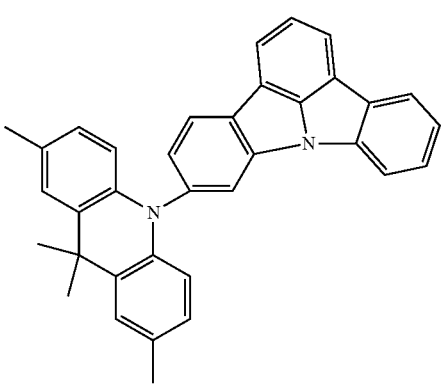
52
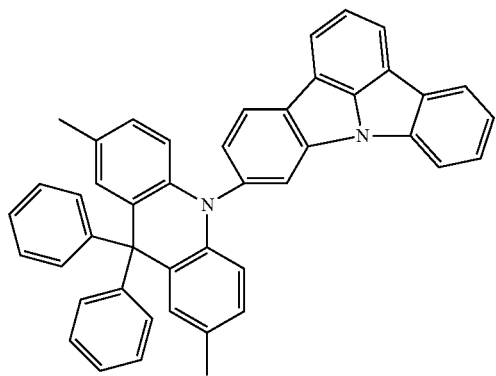
53
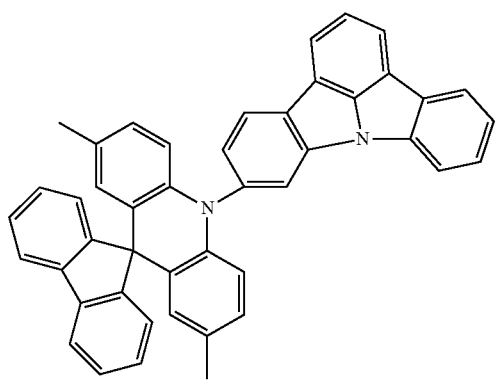

54
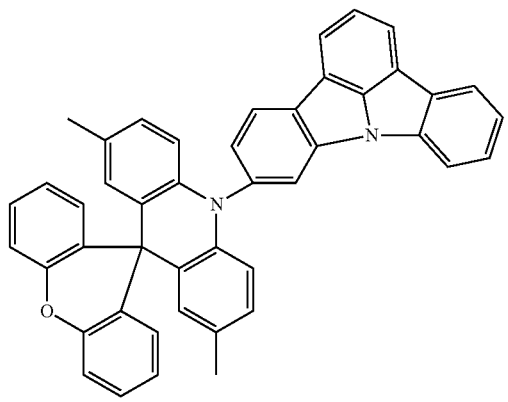
55
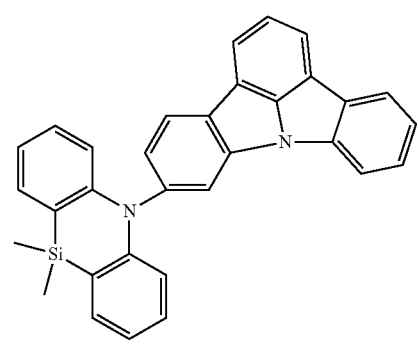
56
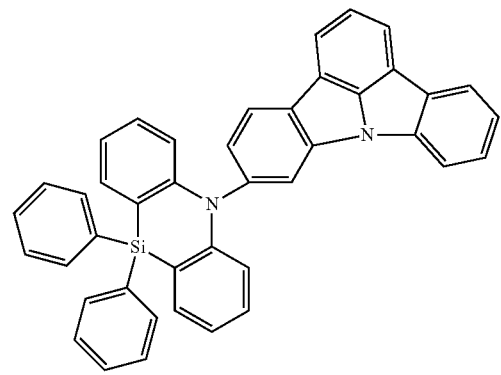
57
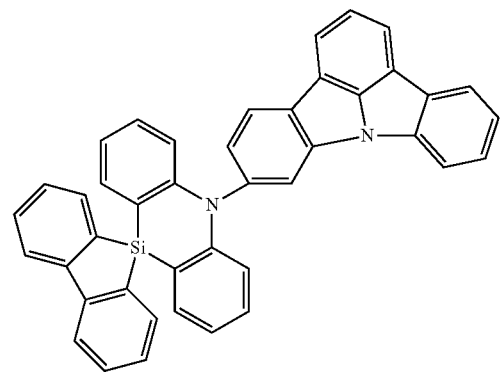
58
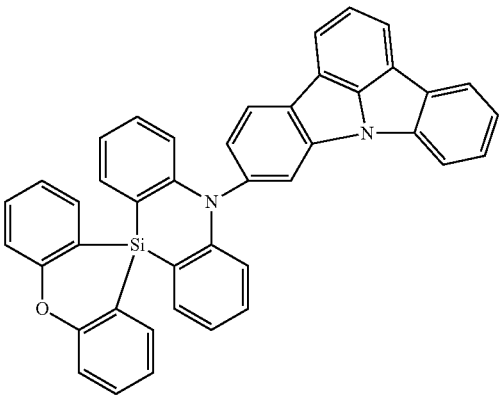
59
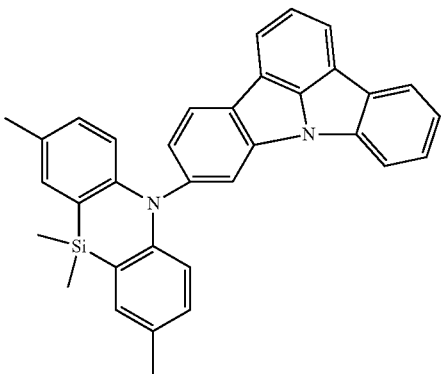
60
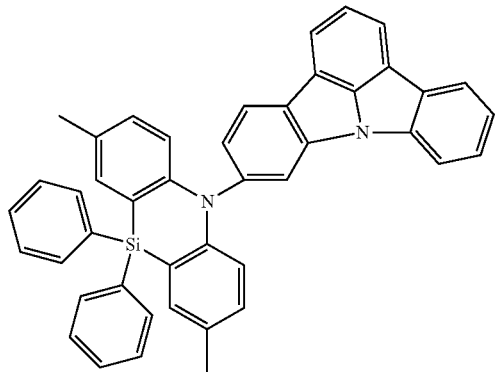
61
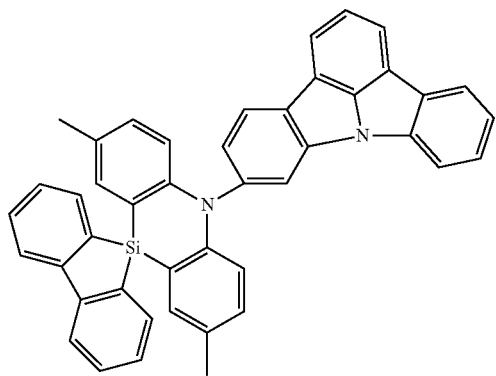

-continued

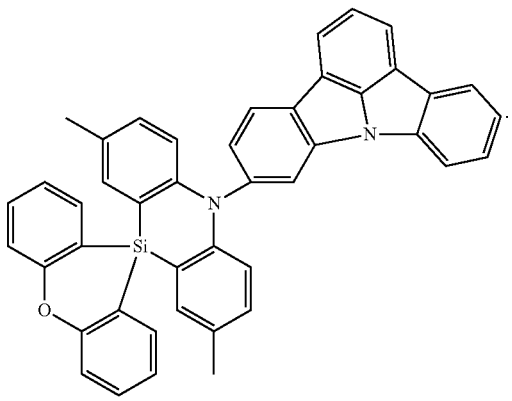

62

12. An organic electroluminescence device, comprising:
a first electrode;
a hole transport region provided on the first electrode;
an emission layer provided on the hole transport region;
an electron transport region provided on the emission layer; and
a second electrode provided on the electron transport region,
wherein the first electrode and the second electrode each independently comprise at least one selected from Ag, Mg, Cu, Al, Pt, Pd, Au, Ni, Nd, Ir, Cr, Li, Ca, LiF/Ca, LiF/Al, Mo, Ti, In, Sn, and Zn, a compound of two or more thereof, a mixture of two or more thereof, and an oxide thereof,
wherein the emission layer includes a heterocyclic compound represented by the following Formula 1, an absolute value of a difference between a singlet energy level and a triplet energy level being about 0.2 eV or less:

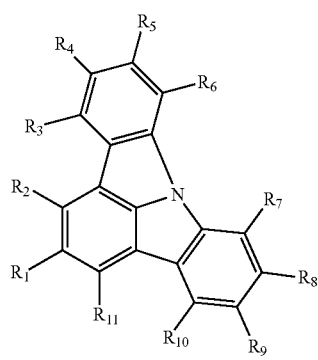

[Formula 1]

wherein in Formula 1,
$R_1$ to $R_{11}$ are each independently a hydrogen atom, a deuterium atom, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, and at least one of $R_1$ to $R_{11}$ is represented by the following Formula 2:

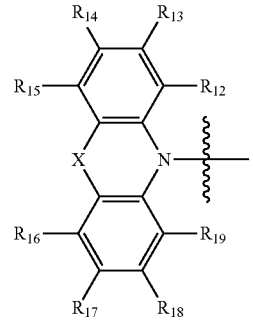

[Formula 2]

wherein in Formula 2,
X is $CY_1Y_2$, $SiY_3Y_4$, $NY_5$, O or S,
$Y_1$ to $Y_5$, and $R_{12}$ to $R_{19}$ are each independently a hydrogen atom, a deuterium atom, a halogen atom, a cyano group, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms,
$Y_1$ and $Y_2$, and $Y_3$ and $Y_4$ may be combined with each other to form a hydrocarbon ring or a heterocycle, and
when X is $C(CH_3)_2$, O or S, the $R_{14}$ and $R_{17}$ are each independently methyl, and $R_{12}$, $R_{13}$, $R_{15}$, $R_{16}$, $R_{18}$, and $R_{19}$ are a hydrogen atom.

13. The organic electroluminescence device as claimed in claim 12, wherein the heterocyclic compound represented by Formula 1 is a material to emit thermally activated delayed fluorescence.

14. The organic electroluminescence device as claimed in claim 12, wherein Formula 2 is represented by one of the following Formulae 2-1 to 2-3:

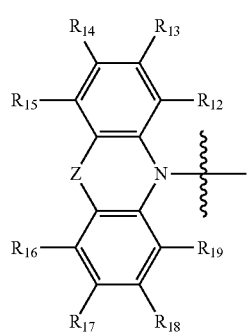

[Formula 2-1]

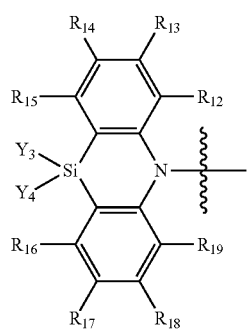

[Formula 2-2]

-continued

[Formula 2-3]

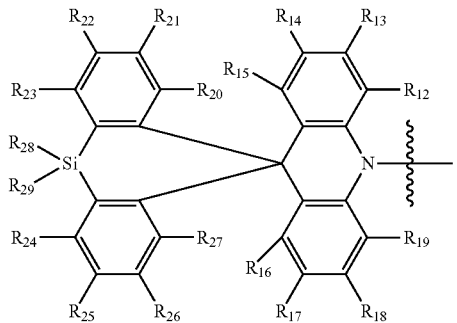

in Formula 2-1,
Z is $CY_1Y_2$, $NY_5$, O, or S,
$R_{12}$ to $R_{19}$, $Y_2$ and $Y_5$ are the same as defined in claim 12,
when Z is $C(CH_3)_2$, O or S, $R_{14}$ and $R_{17}$ are each independently methyl, and $R_{12}$, $R_{13}$, $R_{15}$, $R_{16}$, $R_{18}$, and $R_{19}$ are a hydrogen atom,
in Formula 2-3,
the definition of $R_{20}$ to $R_{29}$ is the same as that of $R_{12}$ to $R_{19}$, and $R_{28}$ and $R_{29}$ may be combined with each other to form a hydrocarbon ring or a heterocycle,
in Formula 2-2 to Formula 2-3,
$R_{12}$ to $R_{19}$, and $Y_1$ to $Y_5$ are the same as defined in claim 12.

15. The electroluminescence device as claimed in claim 12, wherein one of $R_1$, $R_4$, or $R_5$ is represented by the Formula 2.

16. The electroluminescence device as claimed in claim 12, wherein Formula 1 is represented by the following Formula 1-1:

[Formula 1-1]

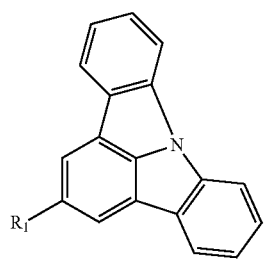

wherein in Formula 1-1, $R_1$ is represented by the Formula 2.

17. The electroluminescence device as claimed in claim 12, wherein Formula 1 is represented by the following Formula 1-2:

[Formula 1-2]

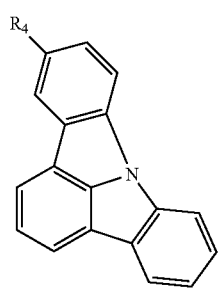

wherein in Formula 1-2, $R_4$ is represented by the Formula 2.

18. The electroluminescence device as claimed in claim 12, wherein Formula 1 is represented by the following Formula 1-3:

[Formula 1-3]

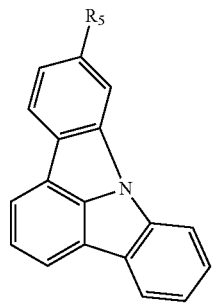

wherein in Formula 1-3, $R_5$ is represented by the Formula 2.

19. The electroluminescence device as claimed in claim 12, wherein Formula 2 is represented by one of the following Formulae 2-4 to 2-10:

[Formula 2-4]

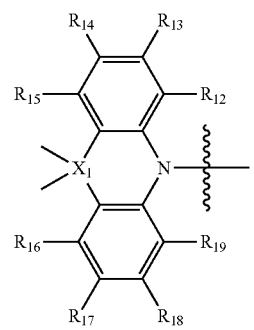

[Formula 2-5]

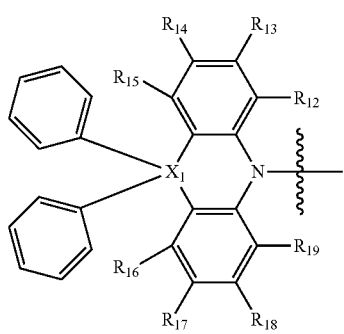

[Formula 2-6]

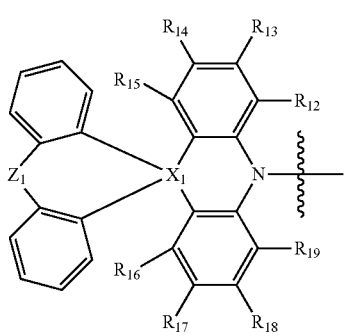

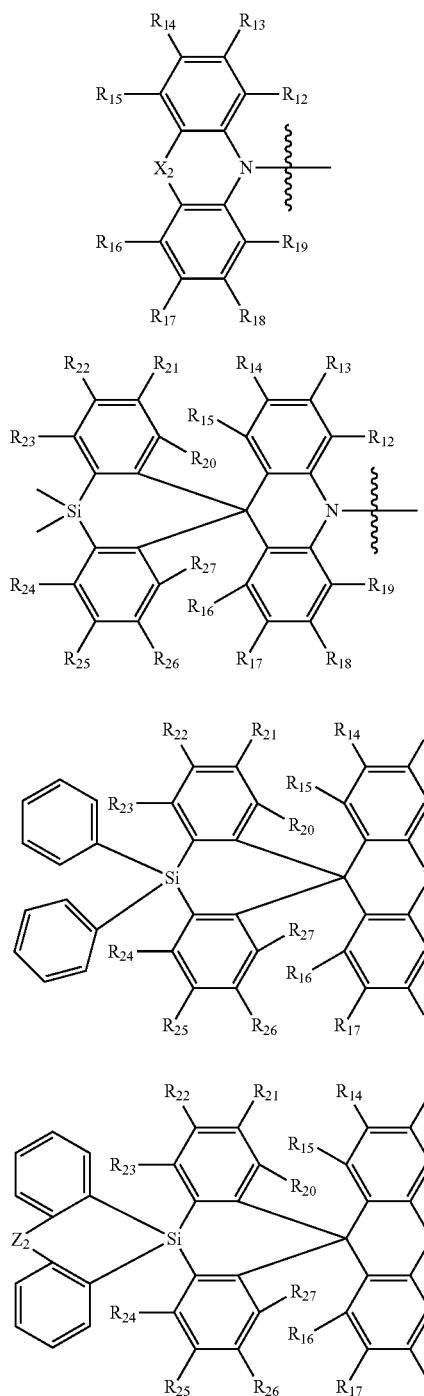

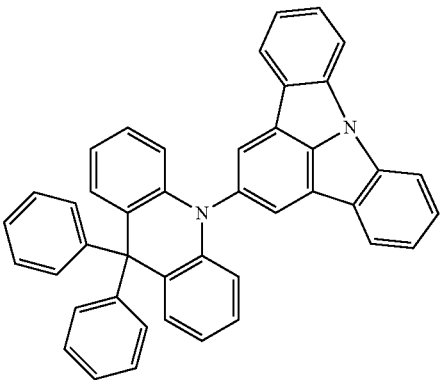

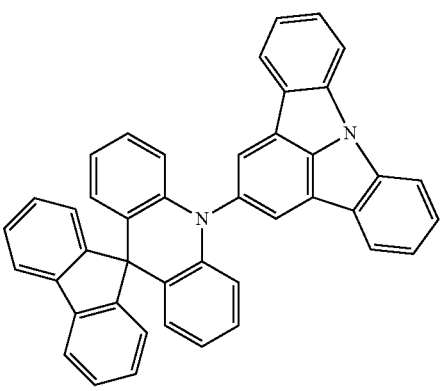

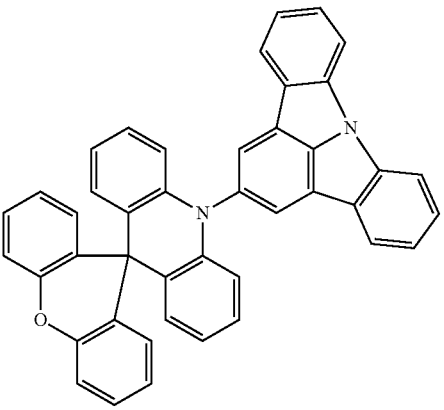

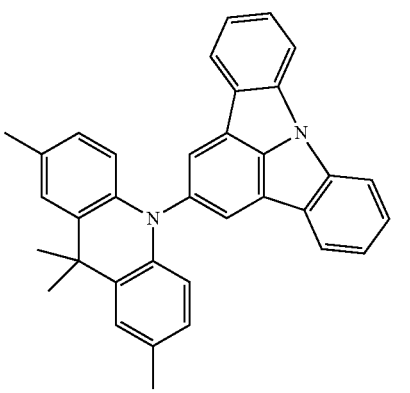

where $X_1$ is C or Si,
$X_2$ is O or S,
$Z_1$ and $Z_2$ are a direct linkage, O, or S,
the definition of $R_{20}$ to $R_{29}$ is the same as that of $R_{12}$ to $R_{19}$,
$R_{12}$ to $R_{19}$ are the same as defined in claim 12,
when $X_1$ is C in Formula 2-4, $R_{14}$ and $R_{17}$ are each independently methyl, and $R_{12}$, $R_{13}$, $R_{15}$, $R_{16}$, $R_{18}$, and $R_{19}$ are a hydrogen atom, and
when $X_2$ is O or S in Formula 2-7, $R_{14}$ and $R_{17}$ are each independently methyl, and $R_{12}$, $R_{13}$, $R_{15}$, $R_{16}$, $R_{18}$, and $R_{19}$ are a hydrogen atom.

20. The electroluminescence device as claimed in claim 12, wherein the heterocyclic compound represented by Formula 1 is one selected from compounds represented in the following Compound Groups 1 to 3:

[Compound Group 1]

6
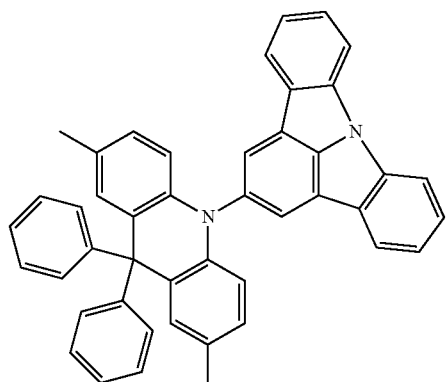
7
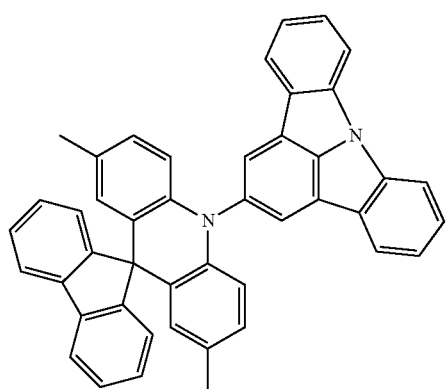
8
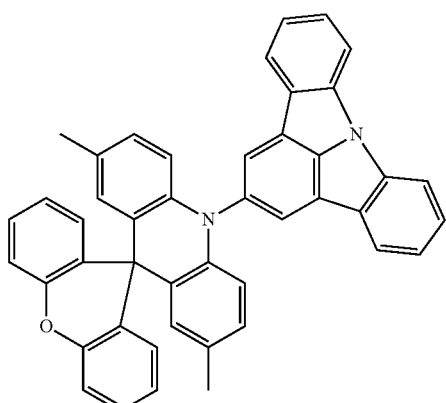
9
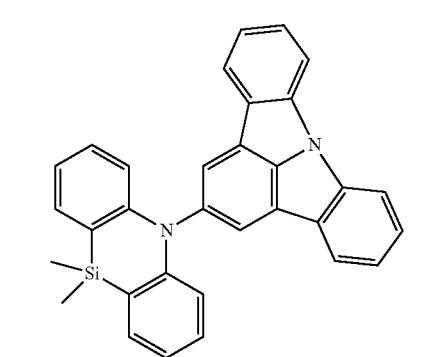
10
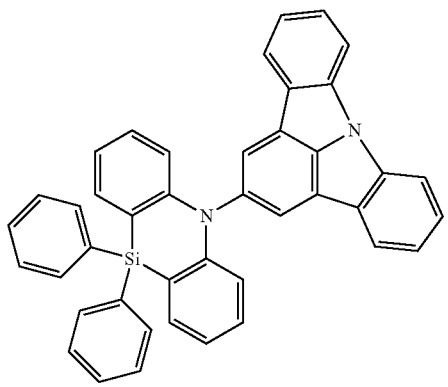
11
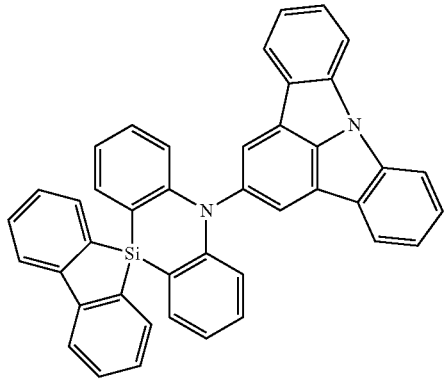
12
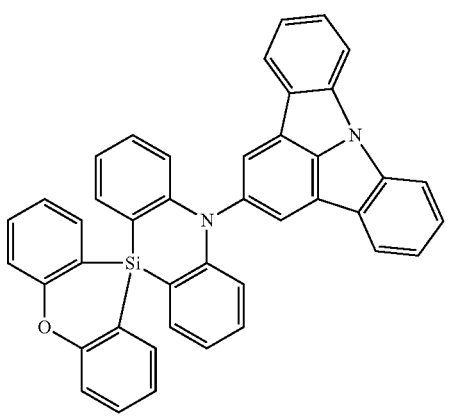
13
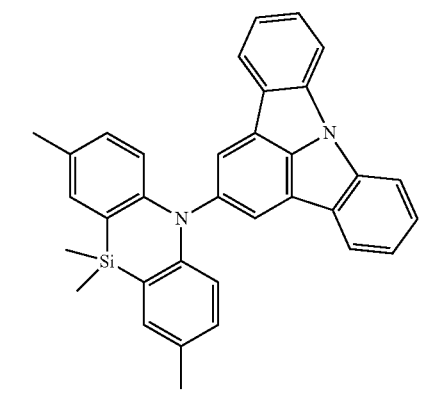

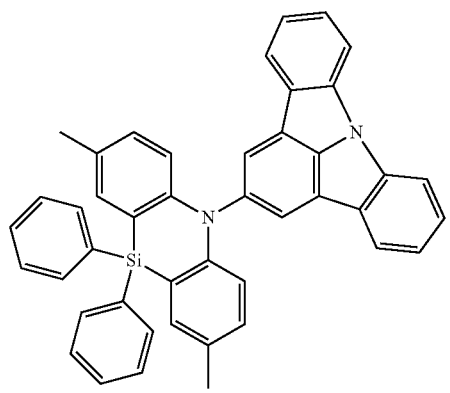
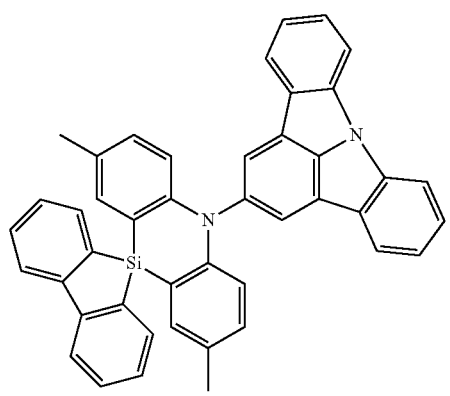
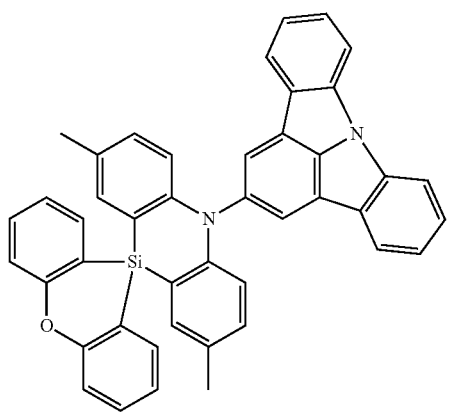
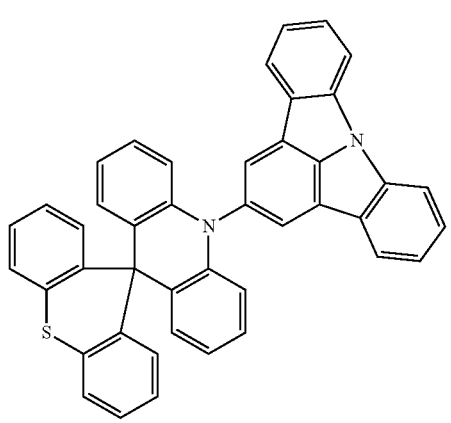
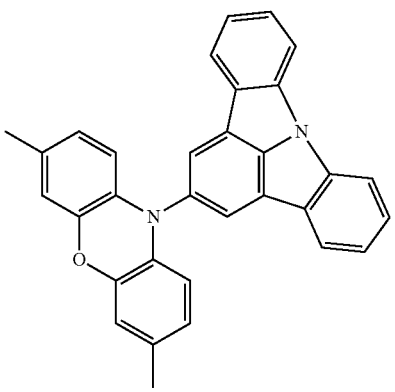
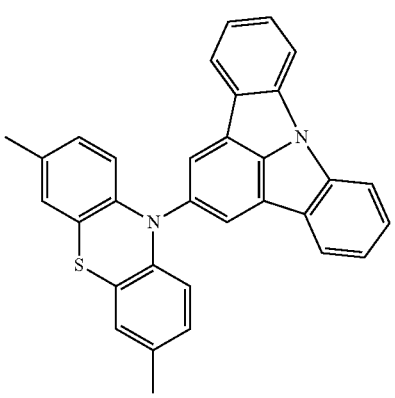
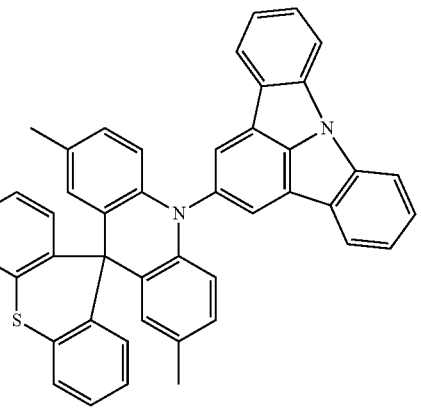
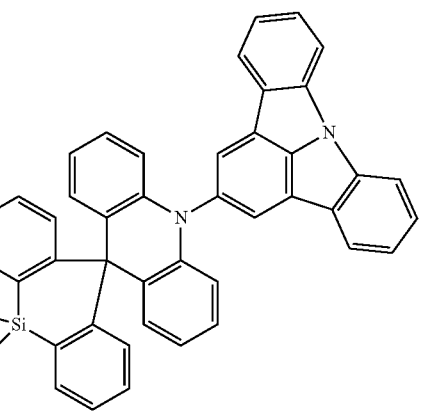

-continued
24
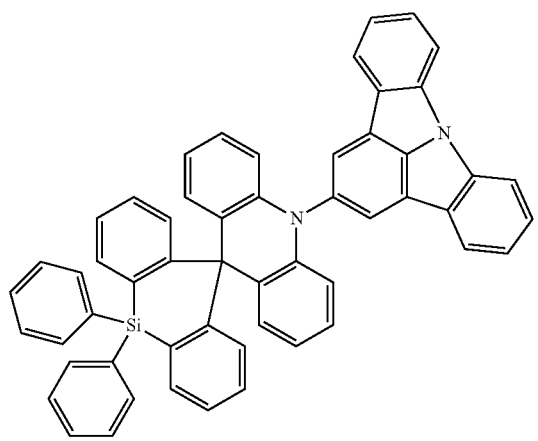
25
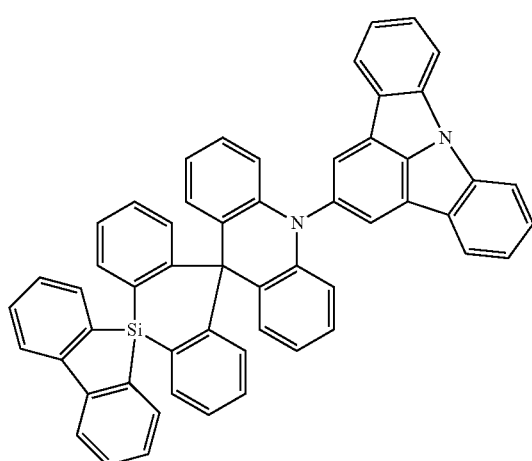
26
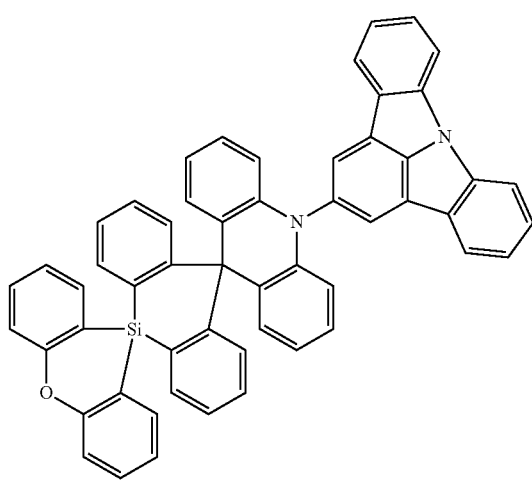
-continued
27
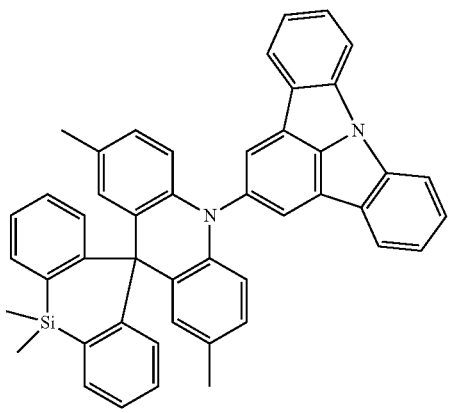
28
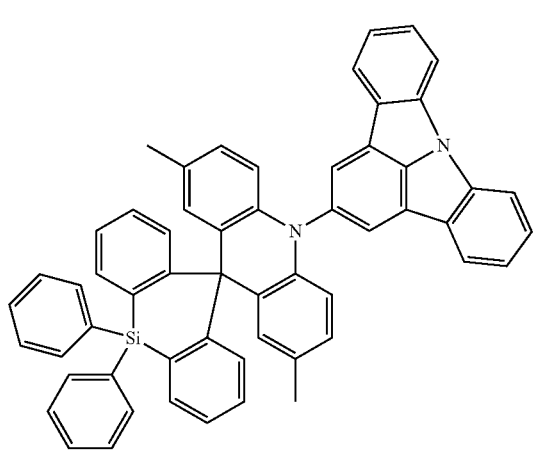
29
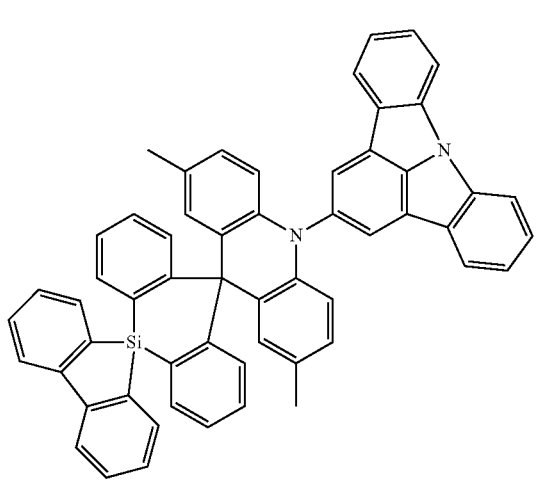

30
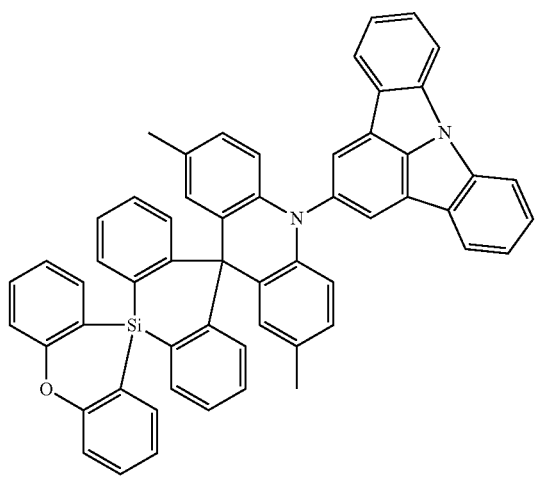
[Compound Group 2]
32
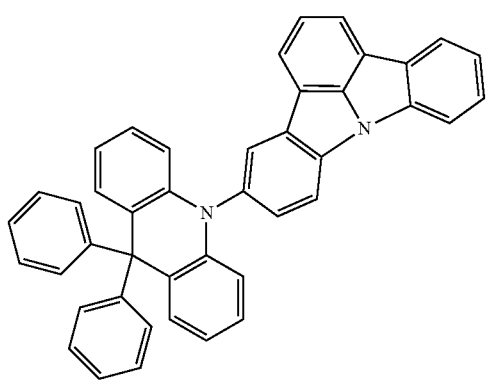
33
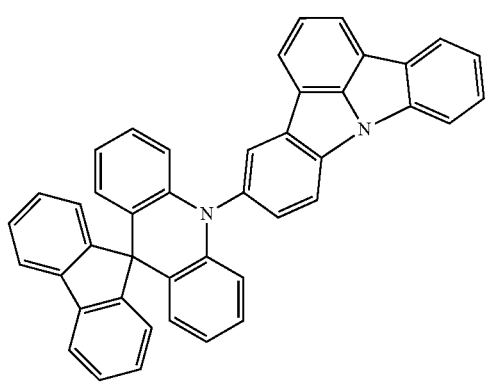
34
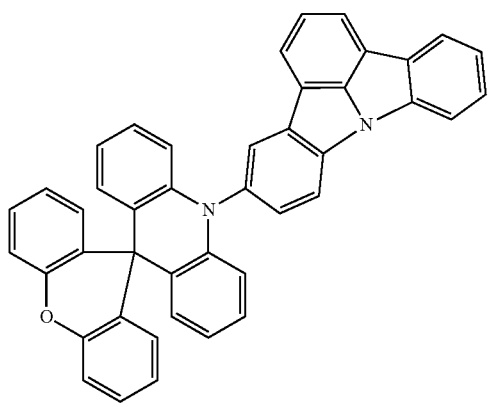
35
36
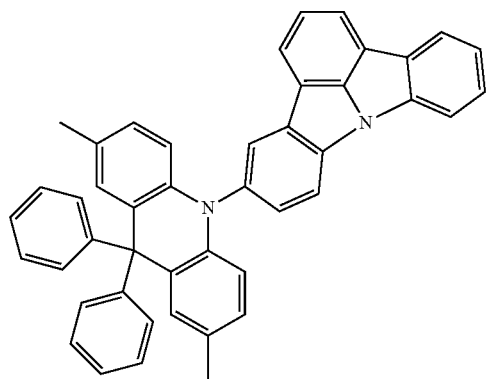
37
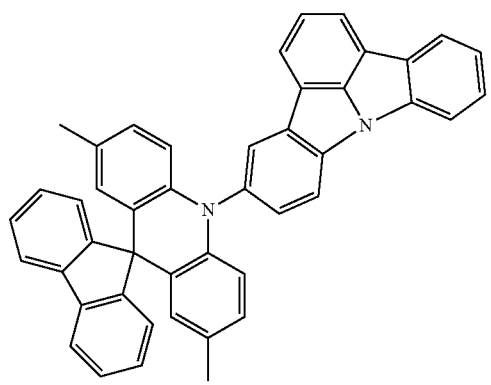

38
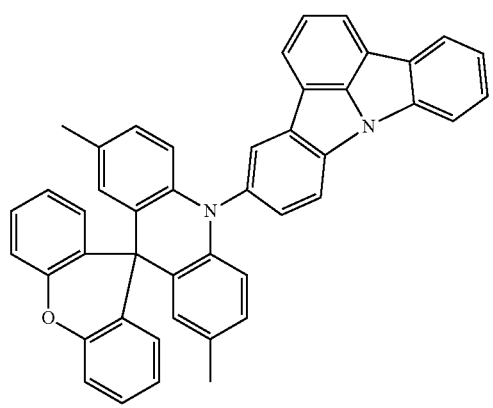
39
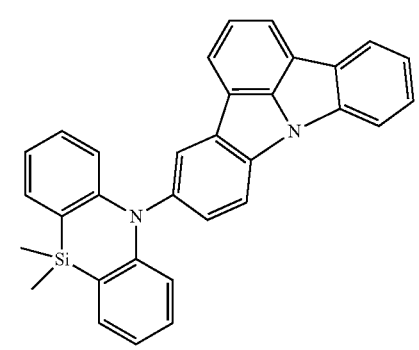
40
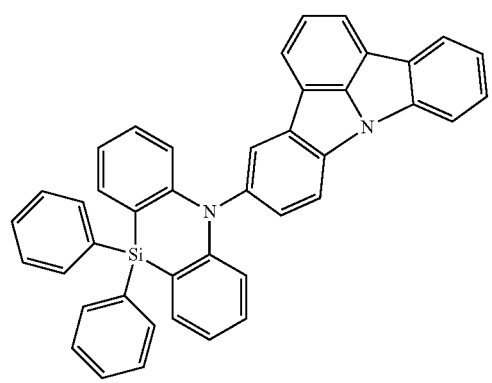
41
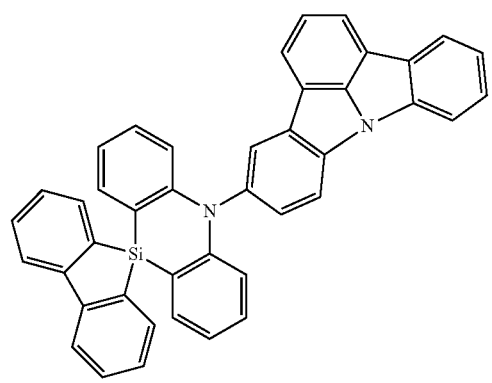
42
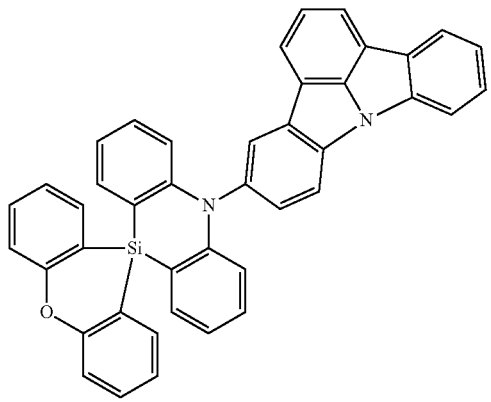
43
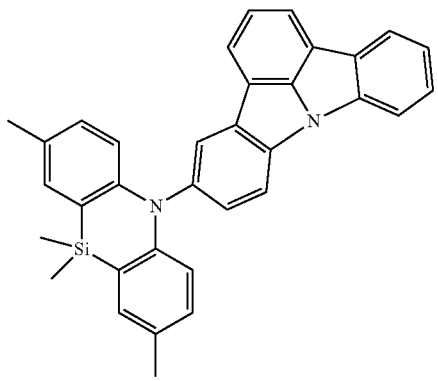
44
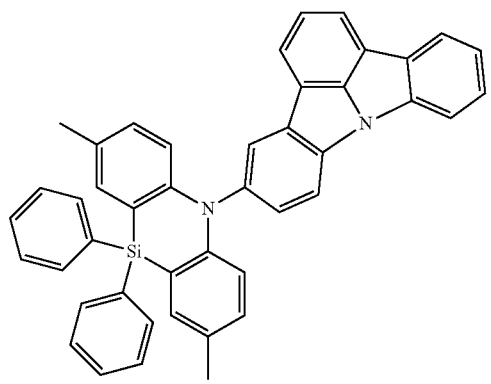
45
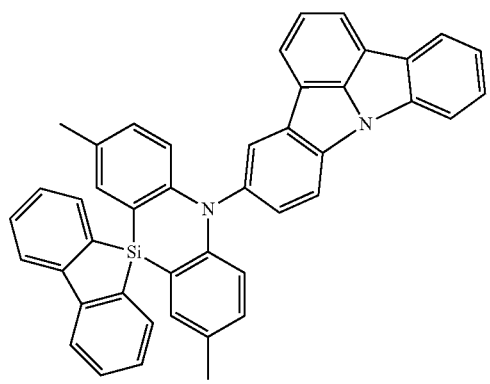

46
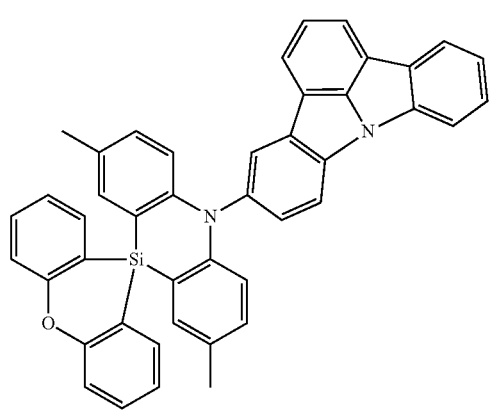
[Compound Group 3]
48
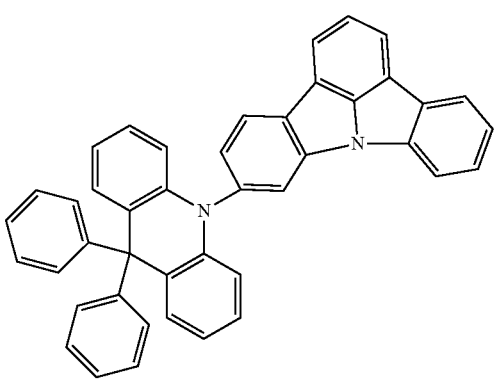
49
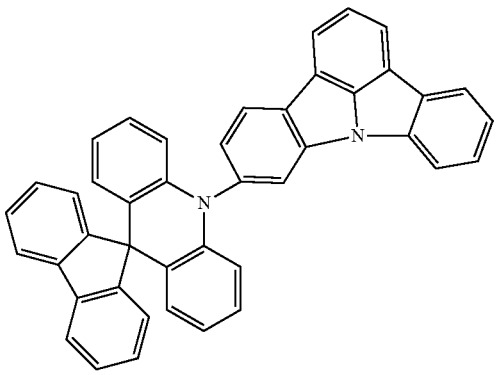
50
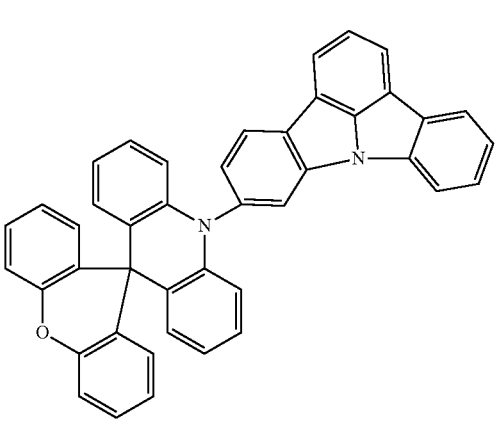
51
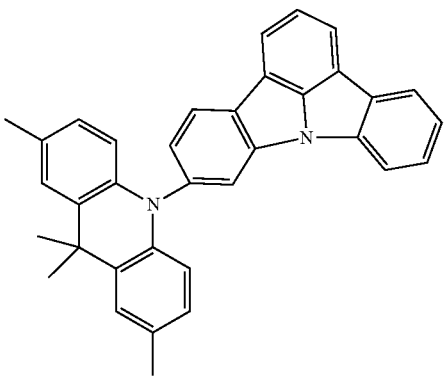
52
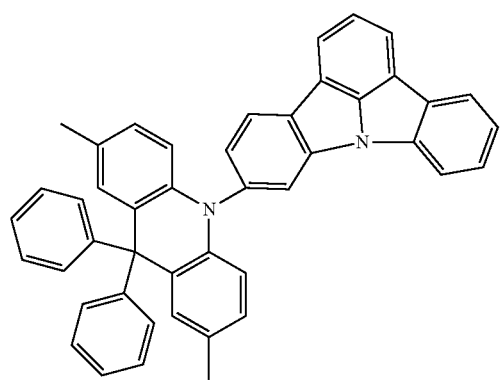
53
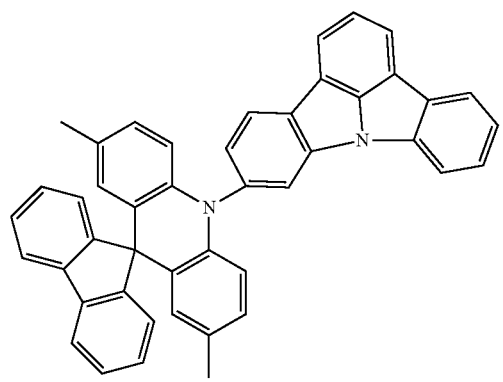
54
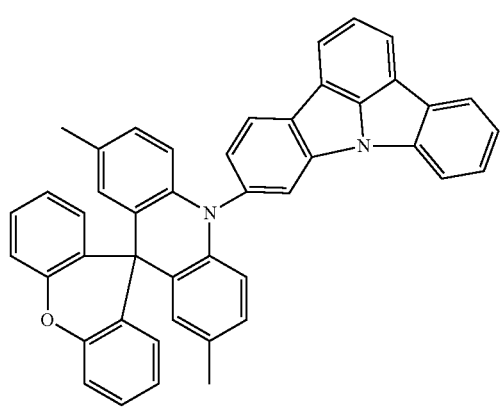

-continued
55
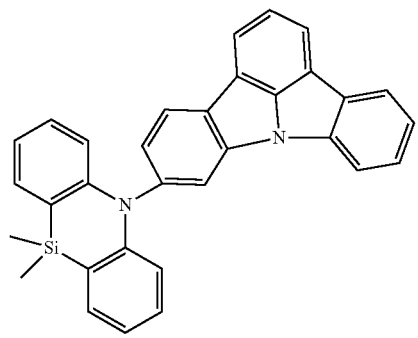
56
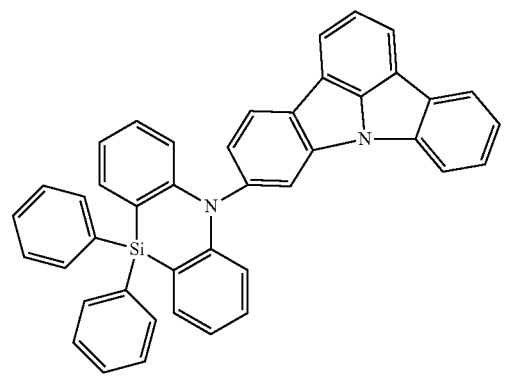
57
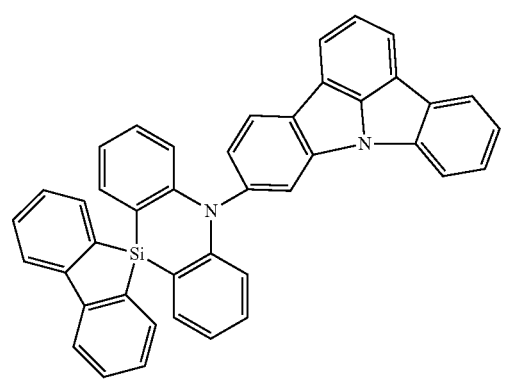
58
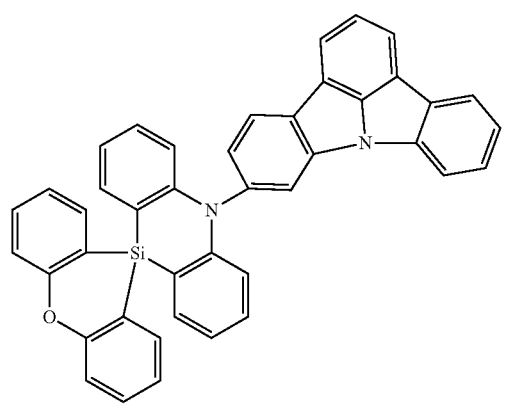
-continued
59
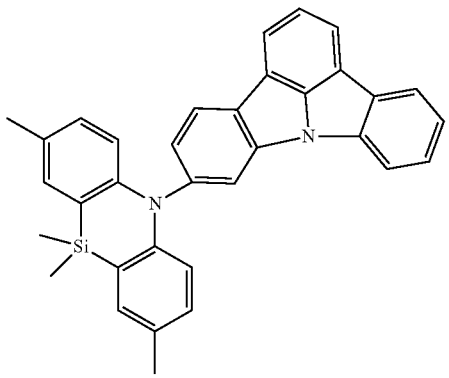
60
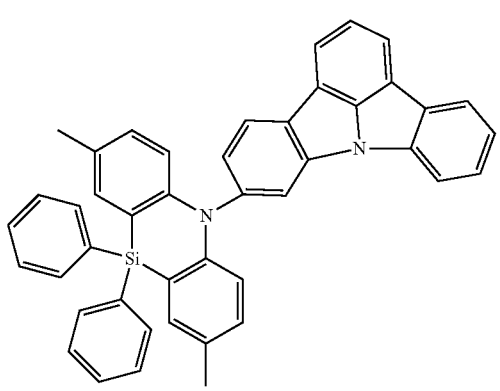
61
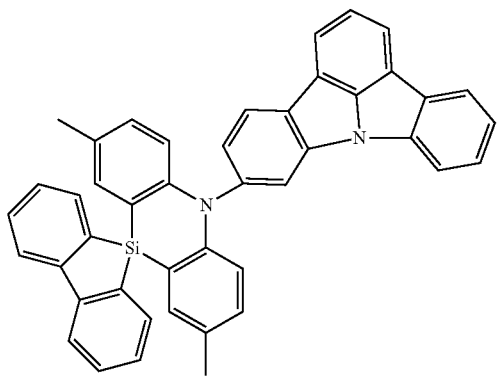
62
* * * * *

UNITED STATES PATENT AND TRADEMARK OFFICE
CERTIFICATE OF CORRECTION

PATENT NO. : 10,862,050 B2
APPLICATION NO. : 15/941061
DATED : December 8, 2020
INVENTOR(S) : Nobutaka Akashi It is certified that error appears in the above-identified patent and that said Letters Patent is hereby corrected as shown below:

In the Claims

Column 46, Line 63, Claim 2      delete "$Y_2$" and insert -- $Y_2$, --

Column 48, Line 67, Claim 7      delete "$R_1$" and insert -- $R_{19}$ --

Column 67, Line 18, Claim 14      delete "$Y_2$" and insert -- $Y_1$, $Y_2$, --

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*